United States Patent
Xiao et al.

(10) Patent No.: US 12,410,441 B2
(45) Date of Patent: Sep. 9, 2025

(54) SYNTHETIC LIVER-TROPIC ADENO-ASSOCIATED VIRUS CAPSIDS AND USES THEREOF

(71) Applicant: The University of North Carolina at Chapel Hill, Chapel Hill, NC (US)

(72) Inventors: Xiao Xiao, Chapel Hill, NC (US); Juan Li, Chapel Hill, NC (US); Bin Xiao, Chapel Hill, NC (US); Zhenhua Yuan, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1087 days.

(21) Appl. No.: 16/972,938

(22) PCT Filed: Jun. 12, 2019

(86) PCT No.: PCT/US2019/036676
§ 371 (c)(1),
(2) Date: Dec. 7, 2020

(87) PCT Pub. No.: WO2019/241324
PCT Pub. Date: Dec. 19, 2019

(65) Prior Publication Data
US 2021/0246467 A1 Aug. 12, 2021

Related U.S. Application Data

(60) Provisional application No. 62/683,868, filed on Jun. 12, 2018.

(51) Int. Cl.
| C12N 15/86 | (2006.01) |
| A61K 48/00 | (2006.01) |
| C07K 14/015 | (2006.01) |
| C12N 7/00 | (2006.01) |

(52) U.S. Cl.
CPC ............. *C12N 15/86* (2013.01); *A61K 48/00* (2013.01); *C07K 14/015* (2013.01); *C12N 7/00* (2013.01); *C12N 2750/14143* (2013.01)

(58) Field of Classification Search
CPC ...................... C12N 15/86; C12N 7/00; C12N 2750/14143; C12N 2750/14122; C12N 2750/14145; C12N 5/067; C12N 2510/00; C12N 2750/14141; C12N 2830/008; A61K 48/00; A61K 48/0075; C07K 14/015; C07K 14/005
See application file for complete search history.

(56) References Cited

U.S. PATENT DOCUMENTS

2011/0104120 A1 5/2011 Xiao et al.

FOREIGN PATENT DOCUMENTS

| CN | 107532173 A | 1/2018 | |
| JP | 2017536116 A | 12/2017 | |
| WO | 2014052789 A1 | 4/2014 | |
| WO | WO-2016081811 A1 * | 5/2016 | ......... A61K 31/7088 |

OTHER PUBLICATIONS

GenBank EU368910.1 (NCBI Reference Accession, EU368910, Adeno-associated virus isolate AAV6.2 capsid protein VP1 gene 2208bp) priority to Jul. 26, 2016. (Year: 2016).*
Nakai et al. "Unrestricted Hepatocyte Transduction with Adeno-Associated Virus Serotype 8 Vectors in Mice" J Virol (2005) 79(1): 214-224 (Year: 2005).*
"International Search Report corresponding to international Application No. PCT/US2019/036676 mailed Oct. 18, 2019".
"NCBI_GenBank_ACB55301.1".
"NCBI_GenBank_ACB55302.1".
"NCBI_GenBank_ACB55303.1".
"NCBI_GenBank_EU368909.1".
"NCBI_GenBank_EU368910.1".
"NCBI_GenBank_EU368911.1".
Ling, Chen , et al., "Prevalence of neutralizing antibodies against liver-tropic adeno-associated virus serotype vectors in 100 healthy Chinese and its potential relation to body constitutions", Journal of Integrative Medicine 13(5):341-346 (Sep. 2015).
"Extended European Search Report corresponding to European Application No. 19820077.6 dated Feb. 23, 2022".
"Recombinant AAV capsid coding sequence, Seq ID No. 10", Database Accession No. BDA63149 (Jul. 14, 2016).
Paulk, Nicole K, et al., "Bioengineered AAV Capsids with Combined High Human Liver Transduction In Vivo and Unique Humoral Seroreactivity", Molecular Therapy 26(1):289-303 (Jan. 1, 2018).
"International Preliminary Report on Patentability corresponding to International Application No. corresponding to International Application No. PCT/US2019/036676 mailed Dec. 24, 2020".
"UniProt, adeno-associated virus 6.2 capsid protein VP1", Accession No. B4Y875 (Dec. 20, 2017).
Lisowski, et al., "Selection and evaluation of clinically relevant AAV variants in a xenograft liver model", Nature 506:382-386 (Feb. 20, 2014).
Vandenberghe, et al., "Naturally occurring singleton residues in AAV capsid impact vector performance and illustrate structural constraints", Gene Ther. 16(12):1416-1428 (Dec. 2009).
Aravalli, et al., "Liver-Targeted Gene Therapy: Approaches and Challenges", Liver Transplantation 21:718-737 (Mar. 14, 2015).
Manno, et al., "Successful transduction of liver in hemophilia by AAV-Factor IX and limitations imposed by the host immune response", Nat. Med. 12(3):342-347 (Mar. 2006).

* cited by examiner

*Primary Examiner* — Neil P Hammell
*Assistant Examiner* — Kelly Nichet Hassell
(74) *Attorney, Agent, or Firm* — Myers Bigel, P.A.

(57) ABSTRACT

The invention relates to synthetic adeno-associated virus capsids targeted to the liver and virus vectors comprising the same. The invention further relates to methods of using the vectors to target the liver and provide liver-specific expression, as well as transduce human primary hepatocytes and cell lines.

35 Claims, 11 Drawing Sheets
Specification includes a Sequence Listing.

TRANSDUCTION OF HUH7 LIVER CANCER CELLS
| | $1 \times 10^5$ VG/CELL | $1 \times 10^4$ VG/CELL |
|---|---|---|
| AAV9-LACZ | 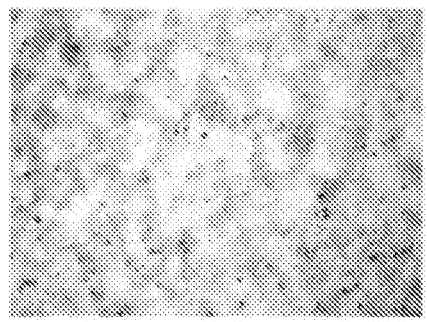 | 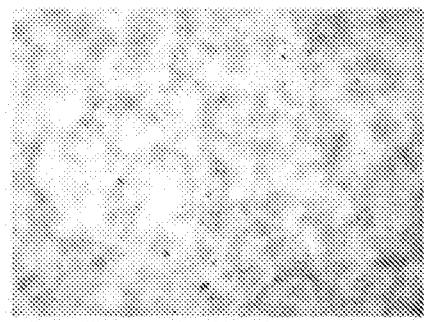 |
| XL12-LACZ | 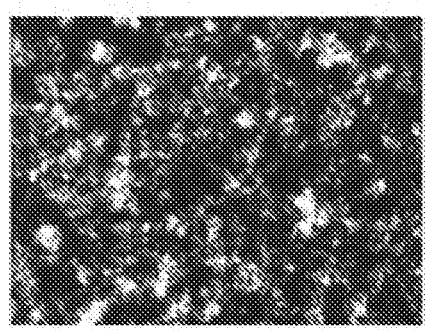 | 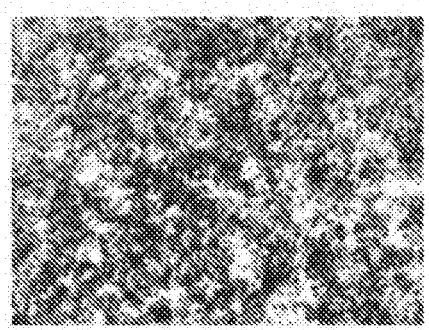 |
| XL32-LACZ | 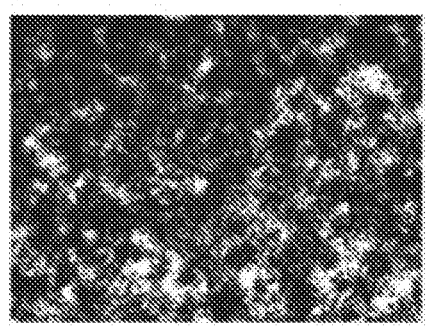 | 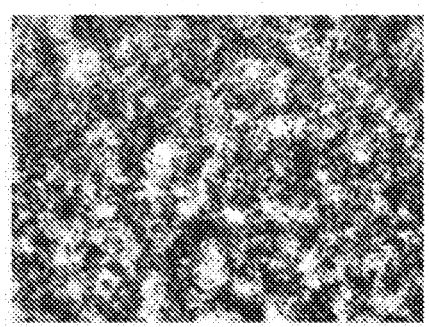 |
*FIG. 2*

AAV-GFP 24 HOURS EXPRESSION HUMAN PRIMARY CELLS
PATIENT #4011
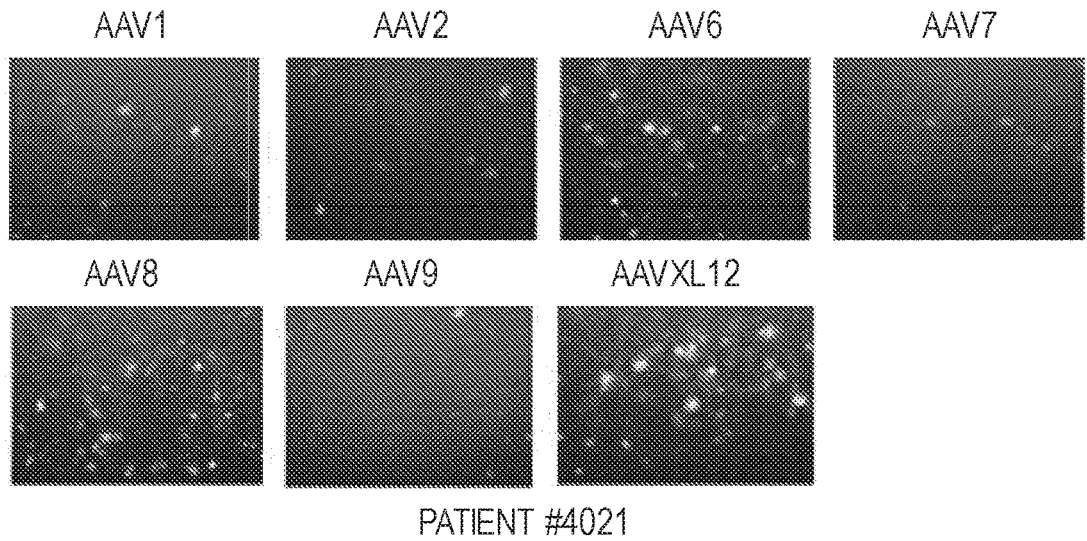
PATIENT #4021
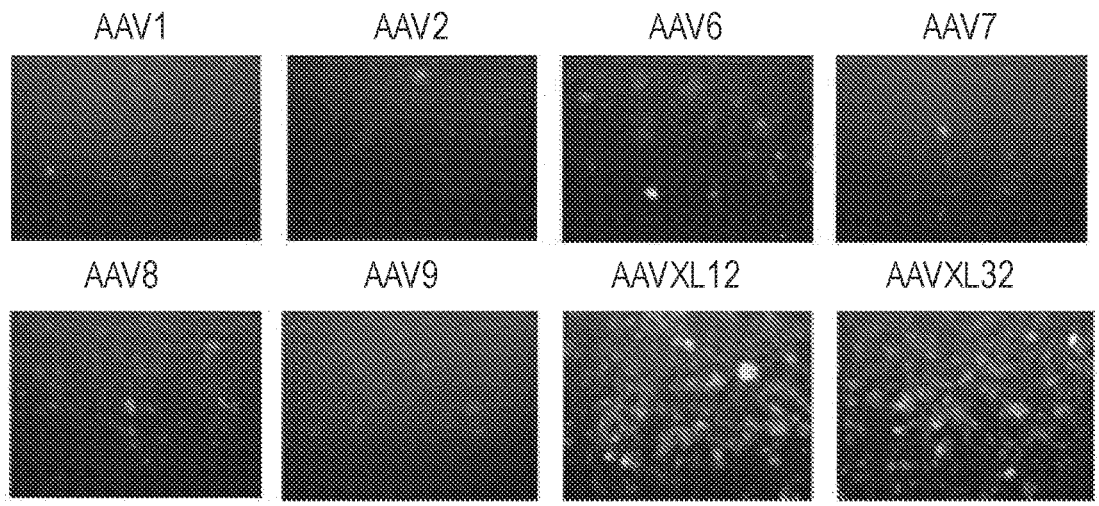
PATIENT #4037
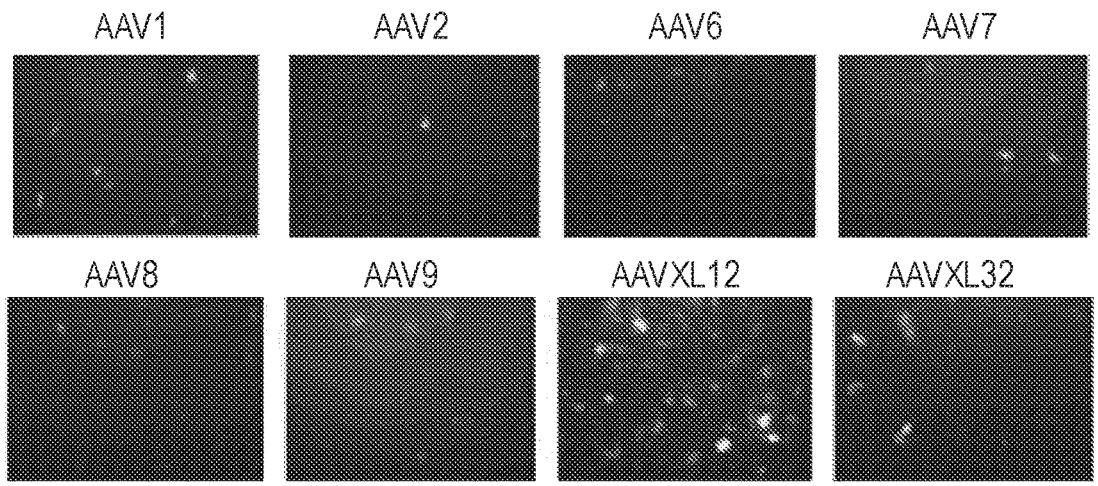
FIG. 3A AAV-GFP 48 HOURS GENE EXPRESSION IN PATIENT
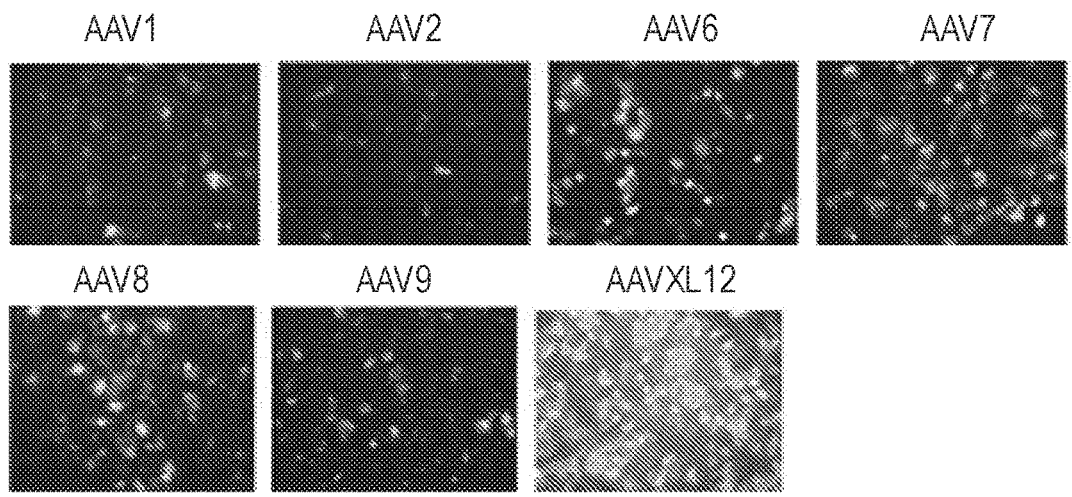
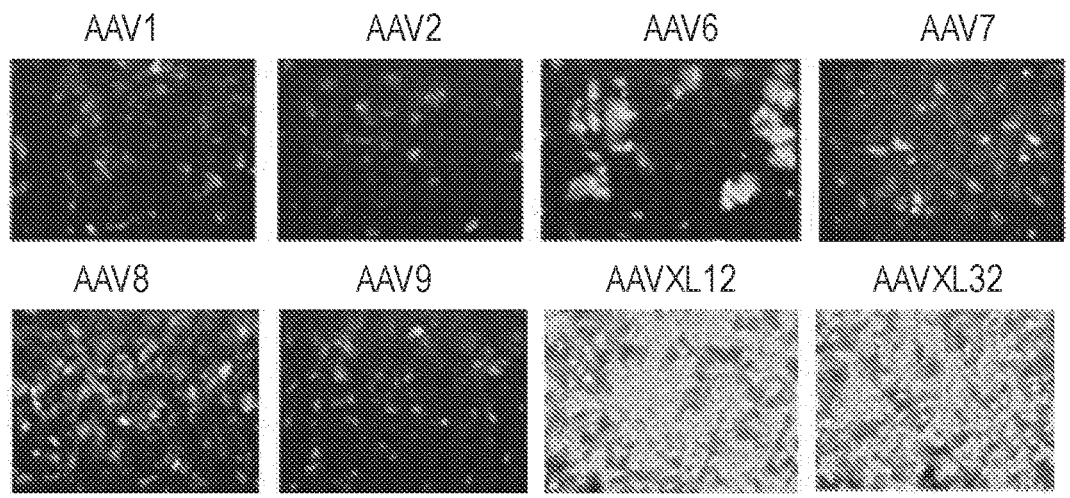
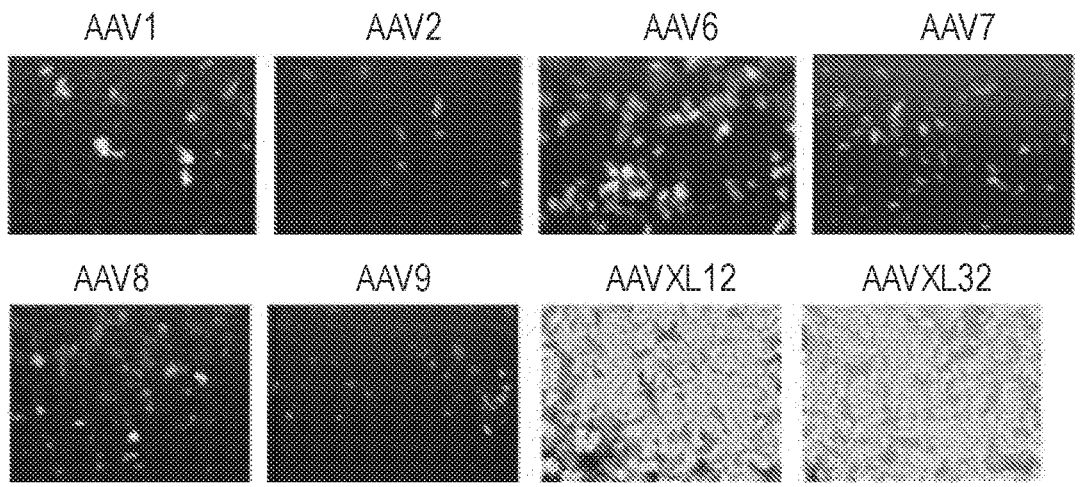
FIG. 3B

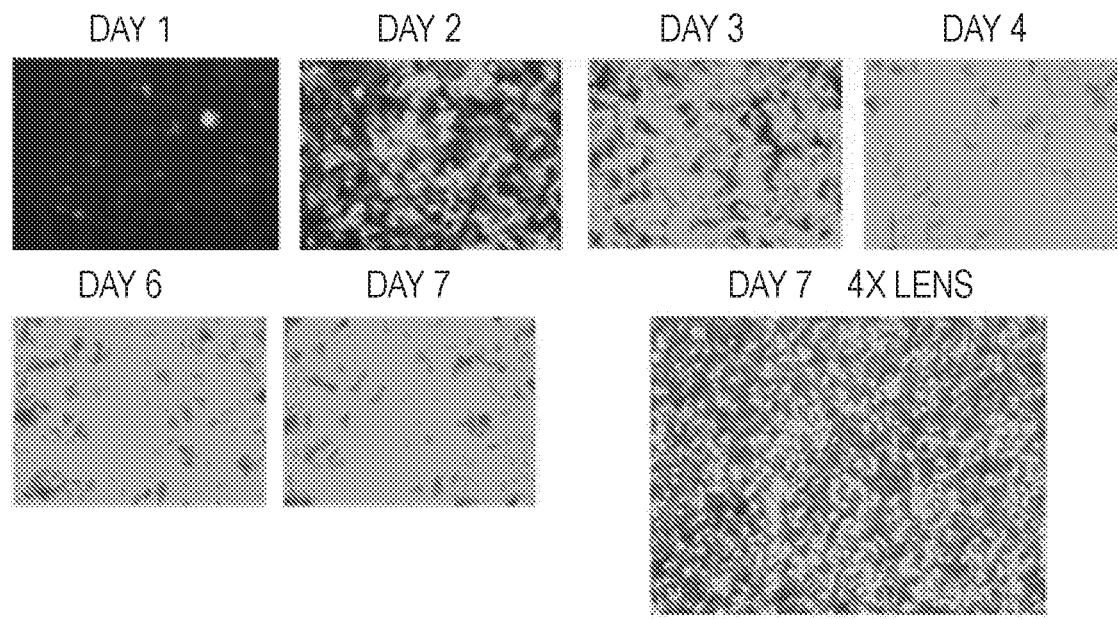
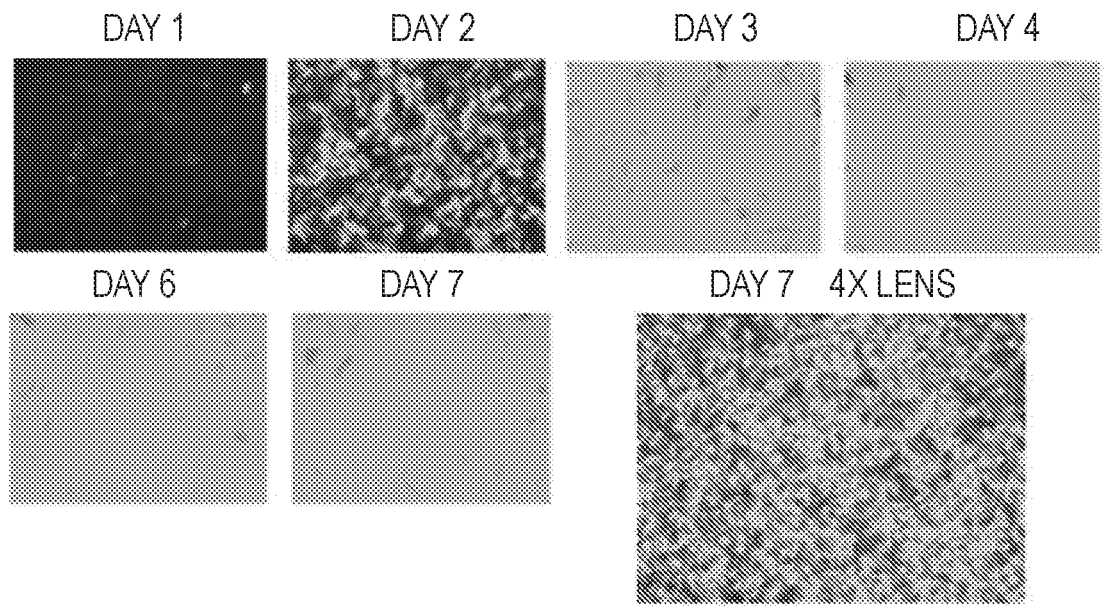
FIG. 3C

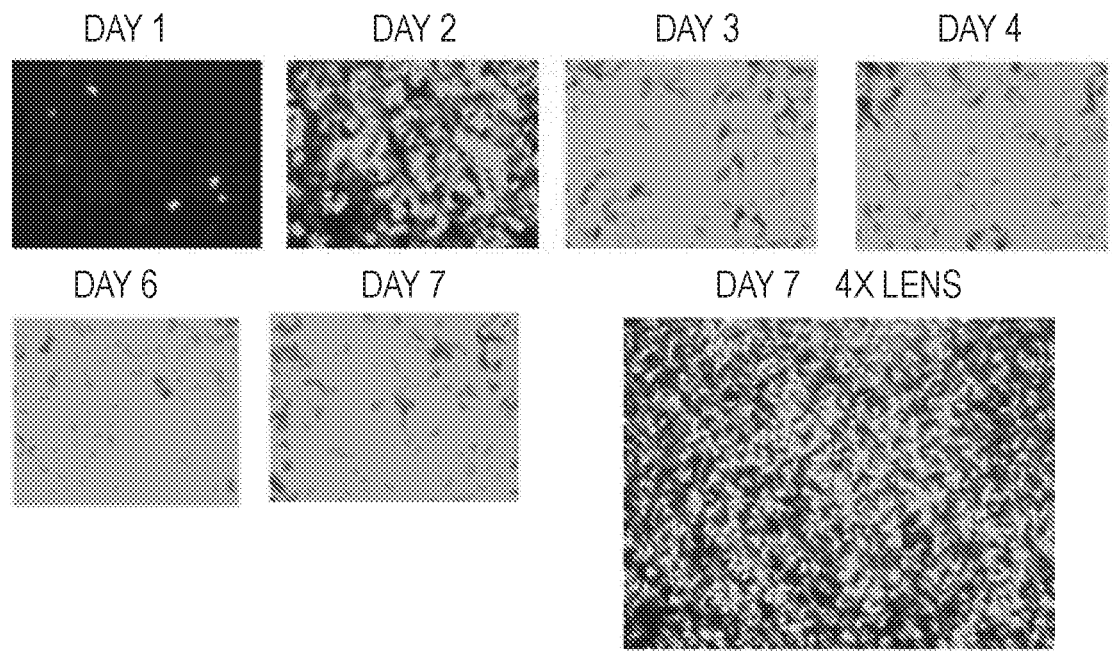
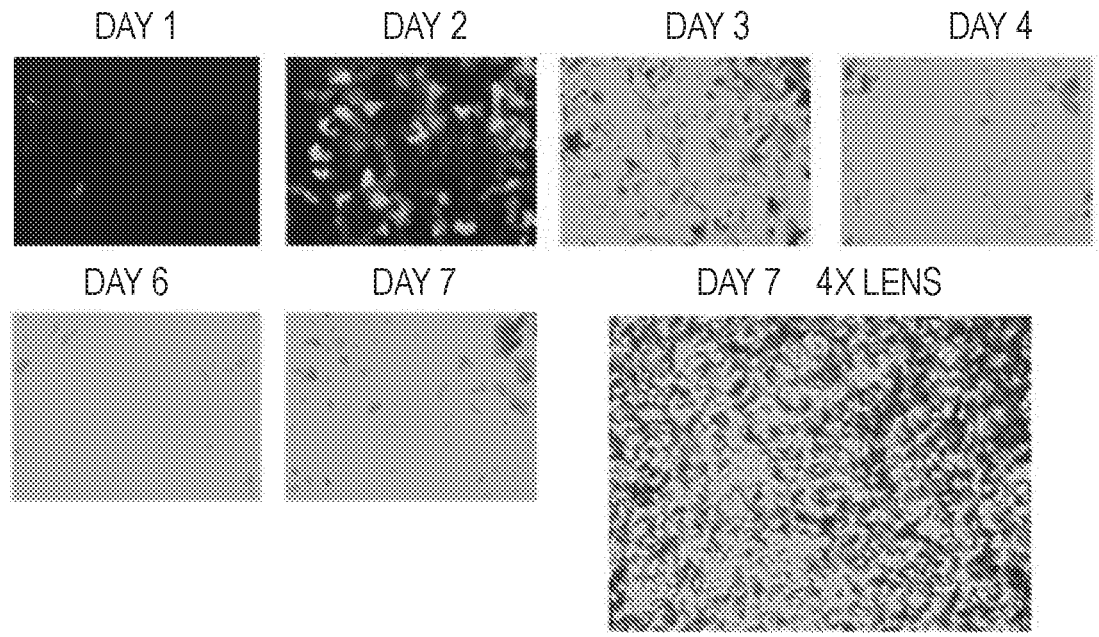
FIG. 3D

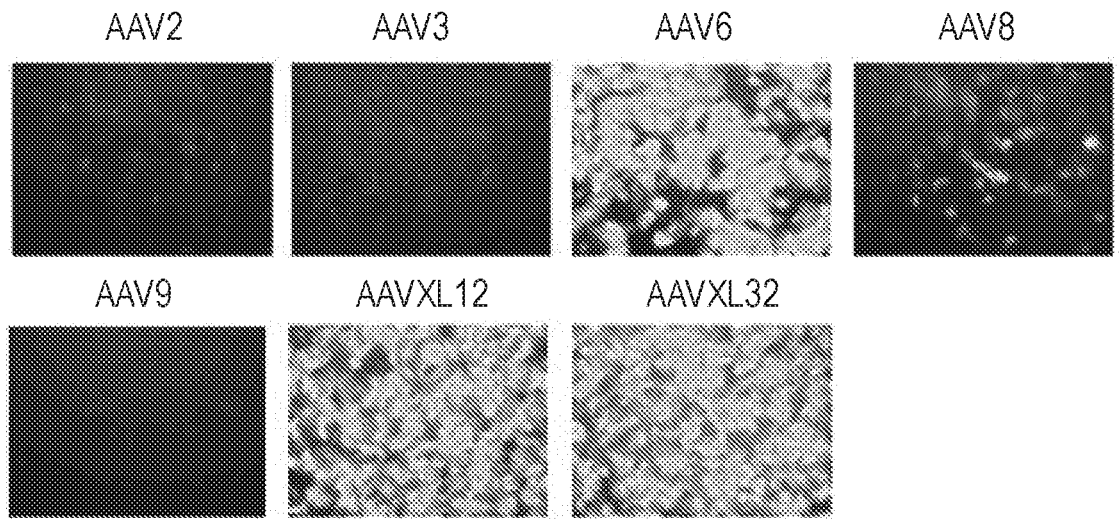
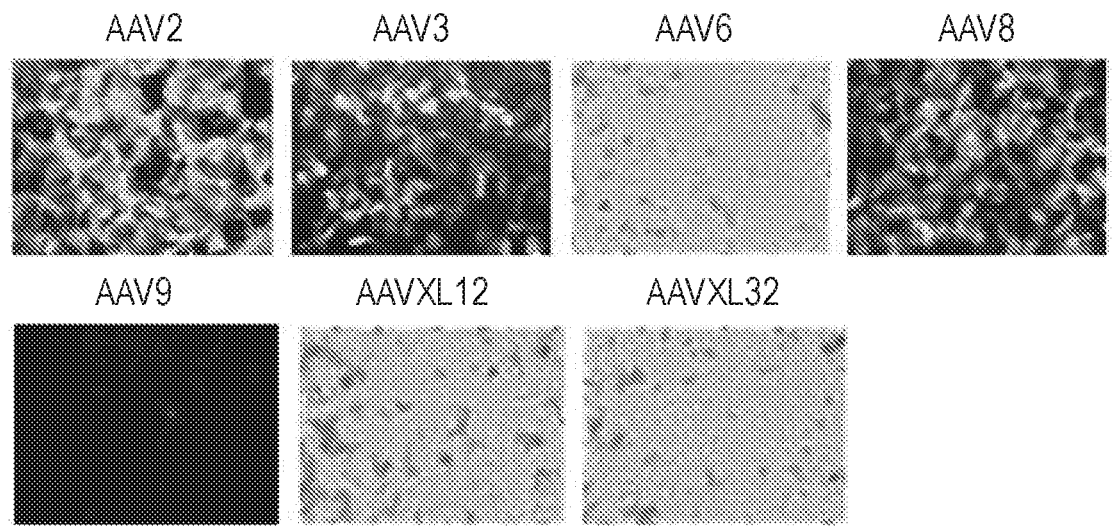
FIG. 4A

AAVXL32-CB-GFP
MONKEY 1
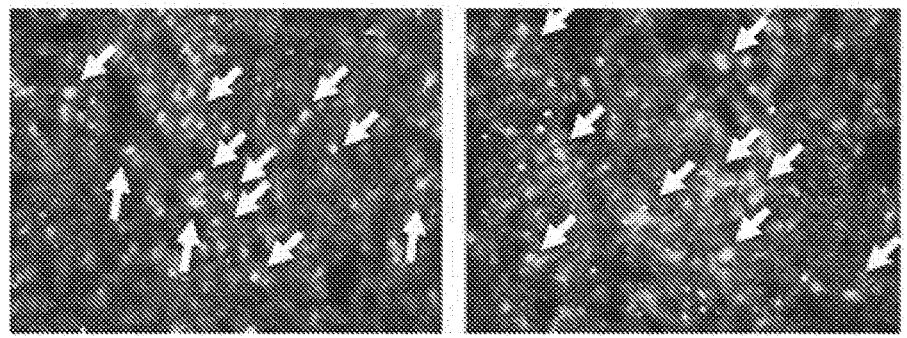
MONKEY 2
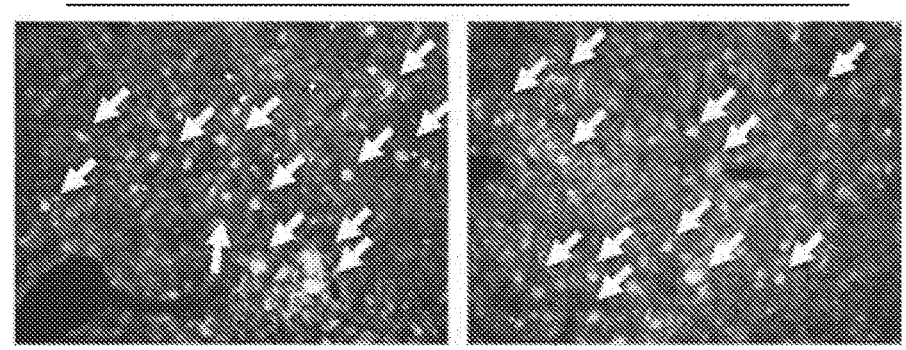
AAV8-CB-GFP
MONKEY 3
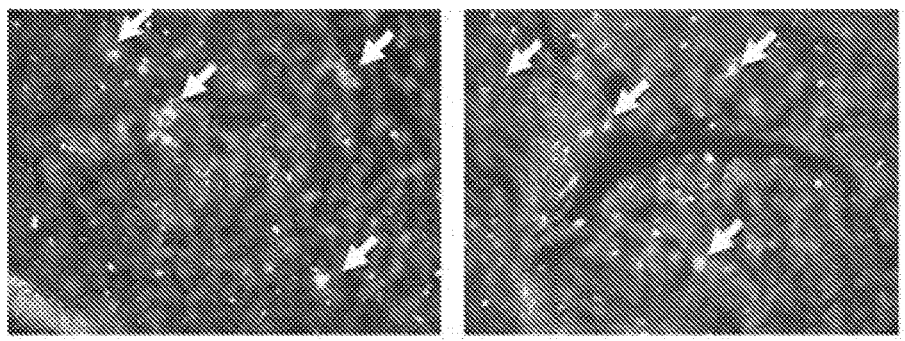
MONKEY 4
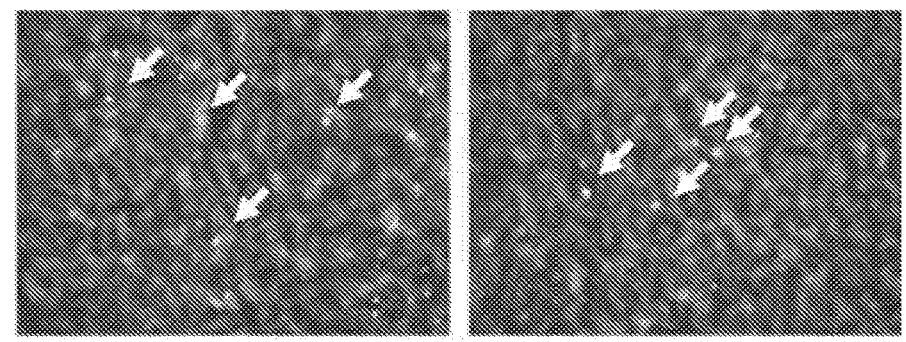
FIG. 5

SYNTHETIC LIVER-TROPIC ADENO-ASSOCIATED VIRUS CAPSIDS AND USES THEREOF

STATEMENT OF PRIORITY

This application is a 35 U.S.C. § 371 national phase application of PCT Application PCT/US2019/036676 filed Jun. 12, 2019, which claims the benefit of U.S. Provisional Application Ser. No. 62/683,868, filed Jun. 12, 2018, the entire contents of each of which are incorporated by reference herein in its entirety.

FIELD OF THE INVENTION

The invention relates to synthetic adeno-associated virus capsids targeted to the liver and virus vectors comprising the same. The invention further relates to methods of using the vectors to target the liver and provide liver-specific expression, as well as transduce human primary hepatocytes and cell lines.

STATEMENT REGARDING ELECTRONIC FILING OF A SEQUENCE LISTING

A Sequence Listing in ASCII text format, submitted under 37 C.F.R. § 1.821, entitled 5470-852_ST25.txt, 28,975 bytes in size, generated on Dec. 4, 2020 and filed via EFS-Web, is provided in lieu of a paper copy. This Sequence Listing is hereby incorporated by reference into the specification for its disclosures.

BACKGROUND OF THE INVENTION

Adeno-associated virus (AAV) is a promising vector for in vivo gene therapy because of its efficient gene transfer and persistent transgene expression in a variety of tissues. The AAV vectors have shown good safety profile and achieved therapeutic effects in gene therapy clinical trials. Some new AAV serotypes were characterized with greatly improved heart, muscle and CNS transduction efficiencies by systemic gene delivery. Some others are effective in liver gene transfer in small animals. These findings shed light on gene therapy of numerous genetic and metabolic diseases. Besides identification of new serotypes, genetic modification could also further improve the AAV vector for its clinical application. One issue in utilizing the AAV vector is its broad tissue tropism, which often results in gene transfer in unwanted tissues and poses potential safety concerns on ectopic gene expression. To improve tissue-specificity and tissue-targeting capacity of the AAV viral particles, random mutagenesis on the capsid genes, in addition to rational engineering, is one of the most powerful ways to enhance capsids diversity and to alter capsids tropisms for intended tissues. Directed evolution such as DNA shuffling is one of the recently developed approaches for genetic engineering of AAV capsid genes.

DNA shuffling is a method of random fragmentation followed by PCR reassembly to introduce or exchange new genetic mutations into the genes by patchy homologous recombination. AAV naturally evolves into different serotypes with variable tissue tropism or immunogenicity. The AAV cap genes of these serotypes are also the ideal templates for generation of novel recombinants by shuffling their DNA and select for the functionally viable mutants and variants. The modified AAV cap genes are cloned into a suitable plasmid vector for production of a chimeric virus library with highly diversified biological properties and for further characterization of their tissue tropism.

A number of in vitro systems based on cultured cell lines have been used for the panning of virus vectors after DNA shuffling. However, in gene therapy applications AAV vectors have to confront more complicated physiological environments in human or animal bodies, e.g., a large number of serum proteins, potential neutralizing and non-neutralizing antibodies, endothelial barriers, the direct tropism and infectivity to the targeted cells, etc. Often, modified vectors that appear to be liver-tropic when tested in vitro do not adequately target the liver when used in vivo.

There is a need in the art for improved liver-tropic AAV vectors that provide benefits for in vivo use.

SUMMARY OF THE INVENTION

The present invention is based, in part, on the use of a strategy where the cap genes of different natural AAV serotypes were dramatically diversified by in vitro recombination using DNA shuffling. The resultant AAV capsid gene libraries containing a broad permutation of mutants and variants were screened directly in vivo in mice first. Considering the barriers for identifying vectors that are effective in vivo, the AAV library the AAV libraries were screened directly in C57BL/6J mice in vivo in the liver to mimic the realistic environment in vivo in preclinical or clinical situations. The preliminarily enriched capsid genes were subsequently selected on cultured cells, for further selection of cell-type and tissue-tropic novel AAV capsids including liver-tropic capsids. One capsid gene was found to be highly enriched in mouse liver and also highly infectious for human liver cancer cell lines and primary human hepatocytes.

Thus, one aspect of the invention relates to a nucleic acid encoding an AAV capsid, the nucleic acid comprising an AAV capsid coding sequence that is at least 90% identical to: (a) the nucleotide sequence of any one of SEQ ID NOS:1-3; or (b) a nucleotide sequence encoding any one of SEQ ID NOS:4-6, along with cells and viral particles comprising the nucleic acid.

Another aspect of the invention relates to an AAV capsid comprising an amino acid sequence at least 90% identical to any one of SEQ ID NOS:4-6, along with AAV particles comprising an AAV vector genome and the AAV capsid of the invention.

A further aspect of the invention relates to a method of producing a recombinant AAV particle comprising an AAV capsid, the method comprising: providing a cell in vitro with a nucleic acid of the invention, an AAV rep coding sequence, an AAV vector genome comprising a heterologous nucleic acid, and helper functions for generating a productive AAV infection; and allowing assembly of the recombinant AAV particle comprising the AAV capsid and encapsidating the AAV vector genome.

An additional aspect of the invention relates to a pharmaceutical formulation comprising the nucleic acid, virus particle, AAV capsid, or AAV particle of the invention in a pharmaceutically acceptable carrier.

Another aspect of the invention relates to a method of delivering a nucleic acid of interest to a hepatocyte, the method comprising contacting the cell with the AAV particle of the invention.

A further aspect of the invention relates to a method of delivering a nucleic acid of interest to a hepatocyte in a mammalian subject, the method comprising administering an effective amount of the AAV particle or pharmaceutical formulation of the invention to a mammalian subject.

Another aspect of the invention relates to a method of treating a disorder in a mammalian subject in need thereof, wherein the disorder is treatable by expressing a product in the liver of the subject, the method comprising administering a therapeutically effective amount of the AAV particle or pharmaceutical formulation of the invention to a mammalian subject.

These and other aspects of the invention are set forth in more detail in the description of the invention below.

BRIEF DESCRIPTION OF THE DRAWINGS

FIG. 2 shows the in vitro comparison of liver-tropic AAV capsids XL12 and XL32 with AAV9 for gene transfer efficiency on the human liver cancer Huh7 cell line. LacZ reporter vectors packaged in AAV9, XL12, and XL32 were used to transduce Huh7 cells at a multiplicity of infections (moi) of $1 \times 10^5$ vg/cell and $1 \times 10^4$ vg/cell. 3 days later, X-gal staining was performed for LacZ expression.

FIGS. 3A-3D show the in vitro comparison of liver-tropic AAV capsids XL12 and XL32 with other serotypes of AAV for gene transfer efficiency on human primary hepatocyte culture. GFP reporter vectors were packaged in AAVXL12, AAVXL32, and multiple other commonly used serotype capsids. The AAV-GFP vectors were used to infect human primary hepatocyte culture at a moi of $1 \times 10^5$ vg/cell. Green fluorescent photography was taken at 24 and 48 hours, or daily up to 7 days. (A) GFP expression at 24 hours post infection with AAV-GFP vectors on human primary hepatocytes from three donors. (B) GFP expression at 48 hours. (C) AAVXL12 and AAVXL32 GFP gene expression 1 to 7 days after infection on hepatocytes of donor patient #4021. (D) AAVXL12 and AAVXL32 GFP gene expression 1 to 7 days after infection on hepatocytes of donor patient #4073. Highly efficient and increasing expression of GFP gene was observed.

FIGS. 4A-4C show the in vitro comparison of liver-tropic AAV capsids XL12 and XL32 with other serotypes of AAV for gene transfer efficiency on canine primary hepatocyte culture. GFP reporter vectors were packaged in AAVXL12, AAVXL32, and multiple other commonly used serotype capsids. The AAV-GFP vectors were used to infect canine primary hepatocyte culture at a moi of $1 \times 10^5$ vg/cell. Green fluorescent photography was take at 24 and 48 hours. (A) GFP expression at 24 and 48 hours on cryopreserved primary hepatocytes (Dog DBCP01). (B) GFP expression at 24 hours on fresh isolated primary hepatocytes (Dog DBF24). (C) GFP expression at 48 hours on fresh isolated primary hepatocytes (Dog DBF24). Highly efficient and increasing expression of GFP gene was observed in AAV6, AAVXL12 and AAVXL32 infected cells.

FIG. 5 shows the comparison of AAVXL32 and AAV8 transduction efficiency in the liver of adult rhesus macaque monkeys by intravenous vector delivery. Adult male Rhesus Macaque monkeys of 3-5 years of age with serum neutralizing antibodies titer lower than 1:8 were injected intravenously with AAV vectors. Two monkeys were injected with AAVXL32-CB-GFP and two injected with AAV-CB-GFP at a dose of $1 \times 10^{12}$ vg/kg body weight. The AAV vector expression cassette was in a double-stranded (also called self-complementary) form for faster and more efficient gene expression. Two weeks later the monkeys were euthanized and liver tissues were taken for cryo-thin-sections and green fluorescent photography. Some GFP positive hepatocytes are highlighted by arrows.

DETAILED DESCRIPTION OF THE INVENTION

Figure 1:
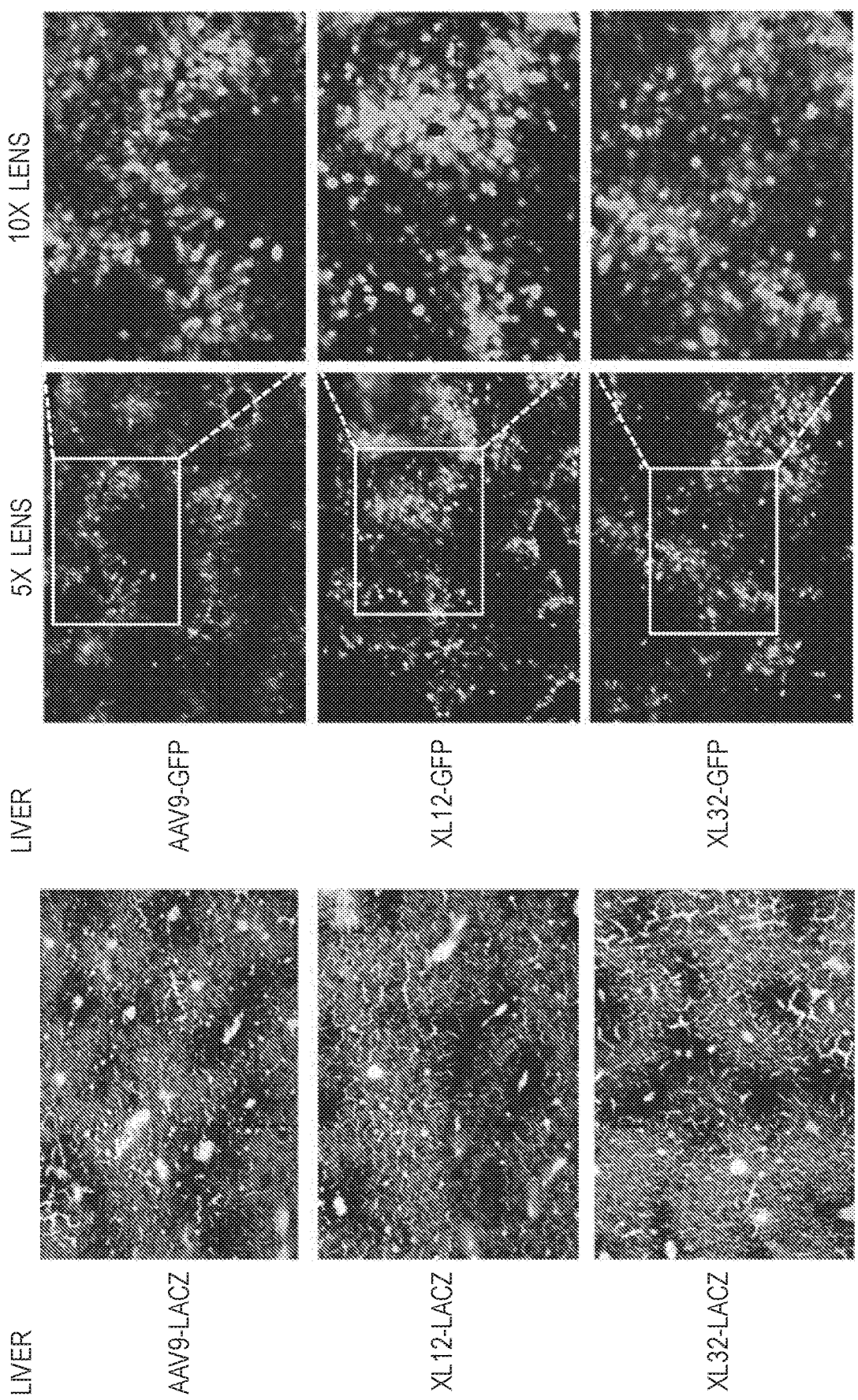
FIGS. 1A-1B show the in vivo comparison of liver-tropic AAV capsids XL12 and XL32 with AAV9 for liver gene transfer efficiency. LacZ and GFP reporter vectors were packaged in AAV9, AAVXL12, and AAVXL32. The vectors were purified, tittered and intravenously injected via the tail vein of adult C57B/6 mice at a dose of $5 \times 10^{12}$ vg (vector genomes)/kg body weight. Three weeks later, mice were sacrificed and liver thin sections stained with X-gal for LacZ expression (FIG. 1A); or directly mounted and fluorescent photography taken for GFP expression (FIG. 1B).

The present invention is based, in part, on the development of synthetic AAV capsid sequences that are capable of transducing hepatocytes in vivo and in vitro. The synthetic capsids can be used to create AAV vectors for use in research or therapeutic applications where liver-specific gene transfer is desired without extensive vector biodistribution to other organs.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of rAAV constructs, modified capsid proteins, packaging vectors expressing the AAV rep and/or cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, NY, 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

I. Definitions

The designation of all amino acid positions in the AAV capsid subunits in the description of the invention and the appended claims is with respect to VP1 capsid subunit numbering.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

The term "consisting essentially of" as used herein in connection with a nucleic acid, protein or capsid structure means that the nucleic acid, protein or capsid structure does not contain any element other than the recited element(s) that significantly alters (e.g., more than about 1%, 5% or 10%) the function of interest of the nucleic acid, protein or capsid structure, e.g., tropism profile of the protein or capsid or a protein or capsid encoded by the nucleic acid.

The term "adeno-associated virus" (AAV) in the context of the present invention includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. See, e.g., BERNARD N. FIELDS et al., VIROLOGY, volume 2, chapter 69 (4th ed., Lippincott-Raven Publishers). A number of additional AAV serotypes and clades have been identified (see, e.g., Gao et al., (2004) J. Virol. 78:6381-6388 and Table 1), which are also encompassed by the term "AAV."

The genomic sequences of various AAV and autonomous parvoviruses, as well as the sequences of the ITRs, Rep proteins, and capsid subunits are known in the art. Such sequences may be found in the literature or in public databases such as the GenBank® database. See, e.g., GenBank® Accession Numbers NC 002077, NC 001401, NC 001729, NC 001863, NC 001829, NC 001862, NC 000883, NC 001701, NC 001510, AF063497, U89790, AF043303, AF028705, AF028704, J02275, J01901, J02275, X01457, AF288061, AH009962, AY028226, AY028223, NC 001358, NC 001540, AF513851, AF513852, AY530579, AY631965, AY631966; the disclosures of which are incorporated herein in their entirety. See also, e.g., Srivistava et al., (1983) *J. Virol.* 45:555; Chiorini et al., (1998) *J. Virol.* 71:6823; Chiorini et al., (1999) *J. Virol.* 73:1309; Bantel-Schaal et al., (1999) *J Virol.* 73:939; Xiao et al., (1999) *J. Virol.* 73:3994; Muramatsu et al., (1996) *Virology* 221:208; Shade et al., (1986) *J Virol.* 58:921; Gao et al., (2002) *Proc. Nat. Acad. Sci. USA* 99:11854; international patent publications WO 00/28061, WO 99/61601, WO 98/11244; U.S. Pat. No. 6,156,303; the disclosures of which are incorporated herein in their entirety. See also Table 1. An early description of the AAV1, AAV2 and AAV3 terminal repeat sequences is provided by Xiao, X., (1996), "Characterization of Adeno-associated virus (AAV) DNA replication and integration," Ph.D. Dissertation, University of Pittsburgh, Pittsburgh, PA (incorporated herein it its entirety).

A "chimeric" AAV nucleic acid capsid coding sequence or AAV capsid protein is one that combines portions of two or more capsid sequences. A "chimeric" AAV virion or particle comprises a chimeric AAV capsid protein.

The term "tropism" as used herein refers to preferential entry of the virus into certain cell or tissue type(s) and/or preferential interaction with the cell surface that facilitates entry into certain cell or tissue types, optionally and preferably followed by expression (e.g., transcription and, optionally, translation) of sequences carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus and/or from a non-integrated episome, as well as any other form which the virus nucleic acid may take within the cell.

TABLE 1

| Complete Genomes | GenBank Accession Number |
| --- | --- |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |

TABLE 1-continued

| Complete Genomes | GenBank Accession Number |
|---|---|
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu43 | AY530606 |
| Hu44 | AY530607 |
| Hu46 | AY530609 |
| Clade B | |
| Hu.19 | AY530584 |
| Hu.20 | AY530586 |
| Hu23 | AY530589 |
| Hu22 | AY530588 |
| Hu24 | AY530590 |
| Hu21 | AY530587 |
| Hu27 | AY530592 |
| Hu28 | AY530593 |
| Hu29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |

TABLE 1-continued

| Complete Genomes | GenBank Accession Number |
|---|---|
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |

TABLE 1-continued

| Complete Genomes | GenBank Accession Number |
|---|---|
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

The term "tropism profile" refers to the pattern of transduction of one or more target cells, tissues and/or organs. Representative examples of synthetic AAV capsids have a tropism profile characterized by efficient transduction of cells of the liver with only low transduction of other organs.

The term "specific for hepatocytes" as used herein refers to a viral vector that, when administered in vivo, preferentially transduces hepatocytes with minimal transduction of cells outside the liver. In some embodiments, at least about 80% of the transduced cells are hepatocytes, e.g., at least about 85%, 90%, 95%, 96%, 97%, 98%, 99% or more hepatocytes.

The term "disorder is treatable by expressing a product in the liver" as used herein refers to a disease, disorder, or injury in which expression of a product (e.g., a protein or polynucleotide) in the liver provides an effective treatment or prevention of the disorder.

As used herein, "transduction" of a cell by a virus vector (e.g., an AAV vector) means entry of the vector into the cell and transfer of genetic material into the cell by the incorporation of nucleic acid into the virus vector and subsequent transfer into the cell via the virus vector.

Unless indicated otherwise, "efficient transduction" or "efficient tropism," or similar terms, can be determined by reference to a suitable positive or negative control (e.g., at least about 50%, 60%, 70%, 80%, 85%, 90%, 95% or more of the transduction or tropism, respectively, of a positive control or at least about 110%, 120%, 150%, 200%, 300%, 500%, 1000% or more of the transduction or tropism, respectively, of a negative control).

Similarly, it can be determined if a virus "does not efficiently transduce" or "does not have efficient tropism" for a target tissue, or similar terms, by reference to a suitable control. In particular embodiments, the virus vector does not efficiently transduce (i.e., does not have efficient tropism for) tissues outside the liver, e.g., muscle, kidney, gonads and/or germ cells. In particular embodiments, undesirable transduction of tissue(s) (e.g., liver) is 20% or less, 10% or less, 5% or less, 1% or less, 0.1% or less of the level of transduction of the desired target tissue(s) (e.g., hepatocytes).

As used herein, the term "polypeptide" encompasses both peptides and proteins, unless indicated otherwise.

A "nucleic acid" or "nucleotide sequence" is a sequence of nucleotide bases, and may be RNA, DNA or DNA-RNA hybrid sequences (including both naturally occurring and non-naturally occurring nucleotide), but is preferably either single or double stranded DNA sequences.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

By the term "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder.

As used herein, the term "prevent," "prevents," or "prevention" (and grammatical equivalents thereof) refers to a delay in the onset of a disease or disorder or the lessening of symptoms upon onset of the disease or disorder. The terms are not meant to imply complete abolition of disease and encompasses any type of prophylactic treatment that reduces the incidence of the condition or delays the onset and/or progression of the condition.

An "effective" or "therapeutically effective" amount as used herein is an amount that is sufficient to provide some improvement or benefit to the subject. Alternatively stated, an "effective" or "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

A "heterologous nucleotide sequence" or "heterologous nucleic acid" is a sequence that is not naturally occurring in the virus. Generally, the heterologous nucleic acid or nucleotide sequence comprises an open reading frame that encodes a polypeptide and/or a nontranslated RNA.

A "therapeutic polypeptide" can be a polypeptide that can alleviate or reduce symptoms that result from an absence or defect in a protein in a cell or subject. In addition, a "therapeutic polypeptide" can be a polypeptide that otherwise confers a benefit to a subject, e.g., anti-cancer effects or improvement in transplant survivability.

As used herein, the term "vector," "virus vector," "delivery vector" (and similar terms) generally refers to a virus particle that functions as a nucleic acid delivery vehicle, and which comprises the viral nucleic acid (i.e., the vector genome) packaged within the virion. Virus vectors according to the present invention comprise a synthetic AAV capsid according to the invention and can package an AAV or rAAV genome or any other nucleic acid including viral nucleic acids. Alternatively, in some contexts, the term "vector," "virus vector," "delivery vector" (and similar terms) may be used to refer to the vector genome (e.g., vDNA) in the absence of the virion and/or to a viral capsid that acts as a transporter to deliver molecules tethered to the capsid or packaged within the capsid.

A "recombinant AAV vector genome" or "rAAV genome" is an AAV genome (i.e., vDNA) that comprises at least one inverted terminal repeat (e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzyczka, (1992) Curr. Topics Microbiol. Immunol. 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3' or 5' end.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The terms "rAAV particle" and "rAAV virion" are used interchangeably here. A "rAAV particle" or "rAAV virion" comprises a rAAV vector genome packaged within an AAV capsid.

The AAV capsid structure is described in more detail in BERNARD N. FIELDS et al., VIROLOGY, volume 2, chapters 69 & 70 (4th ed., Lippincott-Raven Publishers).

By "substantially retain" a property, it is meant that at least about 75%, 85%, 90%, 95%, 97%, 98%, 99% or 100% of the property (e.g., activity or other measurable characteristic) is retained.

II. Synthetic AAV Capsids Targeted to the Liver

The inventors have identified synthetic AAV capsid structures capable of providing transduction of human and other mammalian hepatocytes in vivo and in vitro with minimal tropism for other organs. Thus, one aspect of the invention relates to synthetic AAV capsid structures capable of providing liver gene transfer in a subject, e.g., a wild-type subject. In certain embodiments, the invention relates to a nucleic acid encoding an AAV capsid, the nucleic acid comprising, consisting essentially of, or consisting of an AAV capsid coding sequence that is at least 90% identical to: (a) the nucleotide sequence of any one of SEQ ID NOS:1-3; or (b) a nucleotide sequence encoding any one of SEQ ID NOS:4-6; and viruses comprising the chimeric AAV capsids. In some embodiments, the AAV capsid coding sequence is at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the nucleotide sequence of (a) or (b). In another embodiment, the AAV capsid coding sequence comprises, consist essentially of, or consist of the nucleotide sequence of (a) or (b).

SEQ ID NOS:4-6 show the VP1 capsid protein sequence. The designation of all amino acid positions in the description of the invention and the appended claims is with respect to VP1 numbering. Those skilled in the art will understand that the AAV capsid generally contains the smaller VP2 and VP3 capsid proteins as well. Due to the overlap of the coding sequences for the AAV capsid proteins, the nucleic acid coding sequences and amino acid sequences of the VP2 and VP3 capsid proteins will be apparent from the VP1 sequences shown in the disclosed sequences. In particular, VP2 starts at nucleotide 412 (acg) of SEQ ID NO:1 and threonine 138 of SEQ ID NO:4. VP3 starts at nucleotide 610 (atg) of SEQ ID NO:1 and methionine 204 of SEQ ID NO:4. In certain embodiments, isolated VP2 and VP3 capsid proteins comprising the sequence from SEQ ID NOS:4-6 and isolated nucleic acids encoding the VP2 or VP3 proteins, or both, are contemplated.

The invention also provides synthetic AAV capsid proteins and synthetic capsids, the capsid comprising, consisting essentially of, or consisting of an amino acid sequence that is at least 90% identical to any one of SEQ ID NOS:4-6. In some embodiments, the AAV capsid sequence is at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to any one of SEQ ID NOS:4-6. In some embodiments, the capsid protein comprises, consists essentially of, or consists of an amino acid sequence as shown in SEQ ID NOS:4-6, wherein 1, 2 or fewer, 3 or fewer, 4 or fewer, 5 or fewer, 6 or fewer, 7 or fewer, 8 or fewer, 9 or fewer, 10 or fewer, 12 or fewer, 15 or fewer, 20 or fewer, 25 or fewer, 30 or fewer, 40 or fewer, or 50 or fewer of the amino acids within the capsid protein coding sequence of SEQ ID NOS:4-6 is substituted by another amino acid (naturally occurring, modified and/or synthetic), optionally a conservative amino acid substitution, and/or are deleted and/or there are insertions (including N-terminal and C-terminal extensions) of 1, 2 or fewer, 3 or fewer, 4 or fewer, 5 or fewer, 6 or fewer, 7 or fewer, 8 or fewer, 9 or fewer, 10 or fewer, 12 or fewer, 15 or fewer, 20 or fewer, 25 or fewer, 30 or fewer, 40 or fewer, or 50 or fewer amino acids or any combination of substitutions, deletions and/or insertions, wherein the substitutions, deletions and/or insertions do not unduly impair the structure and/or function of a virion (e.g., an AAV virion) comprising the variant capsid protein or capsid. In some embodiments, the amino acids within the capsid protein coding sequence of SEQ ID NOS:4-6 is substituted by another amino acid at position 220 and/or 643 (numbering with respect to SEQ ID NO: 4). For example, in representative embodiments of the invention, an AAV virion comprising the synthetic capsid protein substantially retains at least one property of a synthetic virion comprising a synthetic capsid protein as shown in SEQ ID NOS:4-6. For example, the virion comprising the synthetic capsid protein can substantially retain the liver tropism profile of a virion comprising the synthetic AAV capsid protein as shown in SEQ ID NOS:4-6. Methods of evaluating biological properties such as virus transduction are well-known in the art (see, e.g., the Examples).

Conservative amino acid substitutions are known in the art. In particular embodiments, a conservative amino acid substitution includes substitutions within one or more of the following groups: glycine, alanine; valine, isoleucine, leucine; aspartic acid, glutamic acid; asparagine, glutamine; serine, threonine; lysine, arginine; and/or phenylalanine, tyrosine.

It will be apparent to those skilled in the art that the amino acid sequences of the chimeric AAV capsid protein of SEQ ID NOS:4-6 can further be modified to incorporate other modifications as known in the art to impart desired properties. As nonlimiting possibilities, the capsid protein can be modified to incorporate targeting sequences (e.g., RGD) or sequences that facilitate purification and/or detection. For example, the capsid protein can be fused to all or a portion of glutathione-S-transferase, maltose-binding protein, a heparin/heparan sulfate binding domain, poly-His, a ligand, and/or a reporter protein (e.g., Green Fluorescent Protein, β-glucuronidase, β-galactosidase, luciferase, etc.), an immunoglobulin Fc fragment, a single-chain antibody, hemagglutinin, c-myc, FLAG epitope, and the like to form a fusion protein. Methods of inserting targeting peptides into the AAV capsid are known in the art (see, e.g., international patent publication WO 00/28004; Nicklin et al., (2001) *Mol. Ther.* 474-181; White et al., (2004) *Circulation* 109:513-319; Muller et al., (2003) *Nature Biotech.* 21:1040-1046.

The viruses of the invention can further comprise a duplexed viral genome as described in international patent publication WO 01/92551 and U.S. Pat. No. 7,465,583.

The invention also provides AAV capsids comprising the synthetic AAV capsid proteins of the invention and virus particles (i.e., virions) comprising the same, wherein the virus particle packages (i.e., encapsidates) a vector genome, optionally an AAV vector genome. In particular embodiments, the invention provides an AAV particle comprising an AAV capsid comprising an AAV capsid protein of the invention, wherein the AAV capsid packages an AAV vector genome. The invention also provides an AAV particle comprising an AAV capsid or AAV capsid protein encoded by the synthetic nucleic acid capsid coding sequences of the invention.

In particular embodiments, the virion is a recombinant vector comprising a heterologous nucleic acid of interest, e.g., for delivery to a cell. Thus, the present invention is useful for the delivery of nucleic acids to cells in vitro, ex vivo, and in vivo. In representative embodiments, the recombinant vector of the invention can be advantageously employed to deliver or transfer nucleic acids to animal (e.g., mammalian) cells.

Any heterologous nucleotide sequence(s) may be delivered by a virus vector of the present invention. Nucleic acids of interest include nucleic acids encoding polypeptides, optionally therapeutic (e.g., for medical or veterinary uses) and/or immunogenic (e.g., for vaccines) polypeptides.

Therapeutic polypeptides include, but are not limited to, cystic fibrosis transmembrane regulator protein (CFTR), dystrophin (including the protein product of dystrophin mini-genes or micro-genes, see, e.g., Vincent et al., (1993) *Nature Genetics* 5:130; U.S. Patent Publication No. 2003017131; Wang et al., (2000) *Proc. Natl. Acad. Sci. USA* 97:13714-9 [mini-dystrophin]; Harper et al., (2002) *Nature Med.* 8:253-61 [micro-dystrophin]); mini-agrin, a laminin-α2, a sarcoglycan (α, β, γ or δ), Fukutin-related protein, myostatin pro-peptide, follistatin, dominant negative myostatin, an angiogenic factor (e.g., VEGF, angiopoietin-1 or 2), an anti-apoptotic factor (e.g., heme-oxygenase-1, TGF-β, inhibitors of pro-apoptotic signals such as caspases, proteases, kinases, death receptors [e.g., CD-095], modulators of cytochrome C release, inhibitors of mitochondrial pore opening and swelling); activin type II soluble receptor, anti-inflammatory polypeptides such as the Ikappa B dominant mutant, sarcospan, utrophin, mini-utrophin, antibodies or antibody fragments against myostatin or myostatin propeptide, cell cycle modulators, Rho kinase modulators such as Cethrin, which is a modified bacterial C3 exoenzyme [available from BioAxone Therapeutics, Inc., Saint-Lauren, Quebec, Canada], BCL-xL, BCL2, XIAP, FLICEc-s, dominant-negative caspase-8, dominant negative caspase-9, SPI-6 (see, e.g., U.S. Patent Application No. 20070026076), transcriptional factor PGC-α1, Pinch gene, ILK gene and thymosin P4 gene), clotting factors (e.g., Factor VIII, Factor IX, Factor X, etc.), erythropoietin, angiostatin, endostatin, catalase, tyrosine hydroxylase, an intracellular and/or extracellular superoxide dismutase, leptin, the LDL receptor, neprilysin, lipoprotein lipase, ornithine transcarbamylase, β-globin, α-globin, spectrin, $α_1$-antitrypsin, methyl cytosine binding protein 2, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, a cytokine (e.g., α-interferon, β-interferon, interferon-γ, interleukins-1 through -14, granulocyte-macrophage colony stimulating factor, lymphotoxin, and the like), peptide growth factors, neurotrophic factors and hormones (e.g., somatotropin, insulin, insulin-like growth factors including IGF-1 and IGF-2, GLP-1, platelet derived growth factor, epidermal growth factor, fibroblast growth factor, nerve growth factor, neurotrophic factor -3 and -4, brain-derived neurotrophic factor, glial derived growth factor, transforming growth factor -α and -β, and the like), bone morphogenic proteins (including RANKL and VEGF), a lysosomal protein, a glutamate receptor, a lymphokine, soluble CD4, an Fc receptor, a T cell receptor, ApoE, ApoC, inhibitor 1 of protein phosphatase inhibitor 1 (I-1), phospholamban, serca2a, lysosomal acid α-glucosidase, α-galactosidase A, Barkct, β2-adrenergic receptor, R2-adrenergic receptor kinase (BARK), phosphoinositide-3 kinase (PI3 kinase), calsarcin, a receptor (e.g., the tumor necrosis growth factor-α soluble receptor), an anti-inflammatory factor such as IRAP, Pim-1, PGC-1a, SOD-1, SOD-2, ECF-SOD, kallikrein, thymosin-β4, hypoxia-inducible transcription factor [HIF], an angiogenic factor, S100A1, parvalbumin, adenylyl cyclase type 6, a molecule that effects G-protein coupled receptor kinase type 2 knockdown such as a truncated constitutively active bARKct; phospholamban inhibitory or dominant-negative molecules such as phospholamban S16E, a monoclonal antibody (including single chain monoclonal antibodies) or a suicide gene product (e.g., thymidine kinase, cytosine deaminase, diphtheria toxin, and tumor necrosis factors such as TNF-α), and any other polypeptide that has a therapeutic effect in a subject in need thereof.

Heterologous nucleotide sequences encoding polypeptides include those encoding reporter polypeptides (e.g., an enzyme). Reporter polypeptides are known in the art and include, but are not limited to, a fluorescent protein (e.g., EGFP, GFP, RFP, BFP, YFP, or dsRED2), an enzyme that produces a detectable product, such as luciferase (e.g., from *Gaussia, Renilla,* or *Photinus*), β-galactosidase, β-glucuronidase, alkaline phosphatase, and chloramphenicol acetyltransferase gene, or proteins that can be directly detected. Virtually any protein can be directly detected by using, for example, specific antibodies to the protein. Additional markers (and associated antibiotics) that are suitable for either positive or negative selection of eukaryotic cells are disclosed in Sambrook and Russell (2001), *Molecular Cloning*, 3rd Ed., Cold Spring Harbor Laboratory Press, Cold Spring Harbor, N.Y., and Ausubel et al. (1992), *Current Protocols in Molecular Biology*, John Wiley & Sons, including periodic updates.

Alternatively, the heterologous nucleic acid may encode a functional RNA, e.g., an antisense oligonucleotide, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487, 6,083,702), interfering RNAs (RNAi) including small interfering RNAs (siRNA) that mediate gene silencing (see, Sharp et al., (2000) *Science* 287:2431), microRNA, or other non-translated "functional" RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi or antisense RNA against the multiple drug resistance (MDR) gene product (e.g., to treat tumors and/or for administration to the heart to prevent damage by chemotherapy), RNAi or antisense RNA against myostatin (Duchenne or Becker muscular dystrophy), RNAi or antisense RNA against VEGF or a tumor immunogen including but not limited to those tumor immunogens specifically described herein (to treat tumors), RNAi or antisense oligonucleotides targeting mutated dystrophins (Duchenne or Becker muscular dystrophy), RNAi or antisense RNA against the hepatitis B surface antigen gene (to prevent and/or treat hepatitis B infection), RNAi or antisense RNA against the HIV tat and/or rev genes (to prevent and/or treat HIV) and/or RNAi or antisense RNA against any other immunogen from a pathogen (to protect a subject from the pathogen) or a defective gene product (to prevent or treat disease). RNAi or antisense RNA against the targets described above or any other target can also be employed as a research reagent.

As is known in the art, anti-sense nucleic acids (e.g., DNA or RNA) and inhibitory RNA (e.g., microRNA and RNAi such as siRNA or shRNA) sequences can be used to induce "exon skipping" in patients with muscular dystrophy arising from defects in the dystrophin gene. Thus, the heterologous nucleic acid can encode an antisense nucleic acid or inhibitory RNA that induces appropriate exon skipping. Those skilled in the art will appreciate that the particular approach to exon skipping depends upon the nature of the underlying defect in the dystrophin gene, and numerous such strategies are known in the art. Exemplary antisense nucleic acids and inhibitory RNA sequences target the upstream branch point and/or downstream donor splice site and/or internal splicing enhancer sequence of one or more of the dystrophin exons (e.g., exons 19 or 23). For example, in particular embodiments, the heterologous nucleic acid encodes an antisense nucleic acid or inhibitory RNA directed against the upstream branch point and downstream splice donor site of exon 19 or 23 of the dystrophin gene. Such sequences can be incorporated into an AAV vector delivering a modified U7 snRNA and the antisense nucleic acid or inhibitory RNA (see, e.g., Goyenvalle et al., (2004) *Science* 306:1796-1799). As another strategy, a modified U1 snRNA can be incorporated into an AAV vector along with siRNA, microRNA or antisense RNA complementary to the upstream and downstream splice sites of a dystrophin exon (e.g., exon 19 or 23) (see, e.g., Denti et al., (2006) *Proc. Nat. Acad. Sci. USA* 103: 3758-3763). Further, antisense nucleic acids and inhibitory RNA can target the splicing enhancer sequences within exons 19, 43, 45 or 53 (see, e.g., U.S. Pat. Nos. 6,653,467; 6,727,355; and 6,653,466).

Ribozymes are RNA-protein complexes that cleave nucleic acids in a site-specific fashion. Ribozymes have specific catalytic domains that possess endonuclease activity (Kim et al., (1987) *Proc. Natl. Acad. Sci. USA* 84:8788; Gerlach et al., (1987) *Nature* 328:802; Forster and Symons, (1987) *Cell* 49:211). For example, a large number of ribozymes accelerate phosphoester transfer reactions with a high degree of specificity, often cleaving only one of several phosphoesters in an oligonucleotide substrate (Michel and Westhof, (1990) *J. Mol. Biol.* 216:585; Reinhold-Hurek and Shub, (1992) *Nature* 357:173). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, (1989) *Nature* 338:217). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of nucleic acid expression may be particularly suited to therapeutic applications (Scanlon et al., (1991) *Proc. Natd. Acad. Sci. USA* 88:10591; Sarver et al., (1990) *Science* 247:1222; Sioud et al., (1992) *J. Mol. Biol.* 223:831).

MicroRNAs (mir) are natural cellular RNA molecules that can regulate the expression of multiple genes by controlling the stability of the mRNA. Over-expression or diminution of a particular microRNA can be used to treat a dysfunction and has been shown to be effective in a number of disease states and animal models of disease (see, e.g., Couzin, (2008) *Science* 319:1782-4). The chimeric AAV can be used to deliver microRNA into cells, tissues and subjects for the treatment of genetic and acquired diseases, or to enhance functionality and promote growth of certain tissues. For example, mir-1, mir-133, mir-206 and/or mir-208 can be used to treat cardiac and skeletal muscle disease (see, e.g., Chen et al., (2006) *Genet.* 38:228-33; van Rooij et al., (2008) *Trends Genet.* 24:159-66). MicroRNA can also be used to modulate the immune system after gene delivery (Brown et al., (2007) *Blood* 110:4144-52).

The term "antisense oligonucleotide" (including "antisense RNA") as used herein, refers to a nucleic acid that is complementary to and specifically hybridizes to a specified DNA or RNA sequence. Antisense oligonucleotides and nucleic acids that encode the same can be made in accordance with conventional techniques. See, e.g., U.S. Pat. No. 5,023,243 to Tullis; U.S. Pat. No. 5,149,797 to Pederson et al.

Those skilled in the art will appreciate that it is not necessary that the antisense oligonucleotide be fully complementary to the target sequence as long as the degree of sequence similarity is sufficient for the antisense nucleotide sequence to specifically hybridize to its target (as defined above) and reduce production of the protein product (e.g., by at least about 30%, 40%, 50%, 60%, 70%, 80%, 90%, 95% or more).

To determine the specificity of hybridization, hybridization of such oligonucleotides to target sequences can be carried out under conditions of reduced stringency, medium stringency or even stringent conditions. Suitable conditions for achieving reduced, medium and stringent hybridization conditions are as described herein.

Alternatively stated, in particular embodiments, antisense oligonucleotides of the invention have at least about 60%, 70%, 80%, 90%, 95%, 97%, 98% or higher sequence identity with the complement of the target sequence and reduce production of the protein product (as defined above).

In some embodiments, the antisense sequence contains 1, 2, 3, 4, 5, 6, 7, 8, 9 or 10 mismatches as compared with the target sequence.

Methods of determining percent identity of nucleic acid sequences are described in more detail elsewhere herein.

The length of the antisense oligonucleotide is not critical as long as it specifically hybridizes to the intended target and reduces production of the protein product (as defined above) and can be determined in accordance with routine procedures. In general, the antisense oligonucleotide is at least about eight, ten or twelve or fifteen nucleotides in length and/or less than about 20, 30, 40, 50, 60, 70, 80, 100 or 150 nucleotides in length.

RNA interference (RNAi) is another useful approach for reducing production of a protein product (e.g., shRNA or siRNA). RNAi is a mechanism of post-transcriptional gene silencing in which double-stranded RNA (dsRNA) corresponding to a target sequence of interest is introduced into a cell or an organism, resulting in degradation of the corresponding mRNA. The mechanism by which RNAi achieves gene silencing has been reviewed in Sharp et al., (2001) *Genes Dev* 15: 485-490; and Hammond et al., (2001) *Nature Rev. Gen.* 2:110-119). The RNAi effect persists for multiple cell divisions before gene expression is regained. RNAi is therefore a powerful method for making targeted knockouts or "knockdowns" at the RNA level. RNAi has proven successful in human cells, including human embryonic kidney and HeLa cells (see, e.g., Elbashir et al., *Nature* (2001) 411:494-8).

Initial attempts to use RNAi in mammalian cells resulted in antiviral defense mechanisms involving PKR in response to the dsRNA molecules (see, e.g., Gil et al., (2000) *Apoptosis* 5:107). It has since been demonstrated that short synthetic dsRNA of about 21 nucleotides, known as "short interfering RNAs" (siRNA) can mediate silencing in mammalian cells without triggering the antiviral response (see, e.g., Elbashir et al., *Nature* (2001) 411:494-8; Caplen et al., (2001) *Proc. Nat. Acad. Sci. USA* 98:9742).

The RNAi molecule (including an siRNA molecule) can be a short hairpin RNA (shRNA; see Paddison et al., (2002), *Proc. Nat. Acad. Sci. USA* 99:1443-1448), which is believed to be processed in the cell by the action of the RNase III like enzyme Dicer into 20-25mer siRNA molecules. The shRNAs generally have a stem-loop structure in which two inverted repeat sequences are separated by a short spacer sequence that loops out. There have been reports of shRNAs with loops ranging from 3 to 23 nucleotides in length. The loop sequence is generally not critical. Exemplary loop sequences include the following motifs: AUG, CCC, UUCG, CCACC, CTCGAG, AAGCUU, CCACACC and UUCAAGAGA.

The RNAi can further comprise a circular molecule comprising sense and antisense regions with two loop regions on either side to form a "dumbbell" shaped structure upon dsRNA formation between the sense and antisense regions. This molecule can be processed in vitro or in vivo to release the dsRNA portion, e.g., a siRNA.

International patent publication WO 01/77350 describes a vector for bi-directional transcription to generate both sense and antisense transcripts of a heterologous sequence in a eukaryotic cell. This technique can be employed to produce RNAi for use according to the invention.

Shinagawa et al., (2003) *Genes Dev.* 17:1340 reported a method of expressing long dsRNAs from a CMV promoter (a pol II promoter), which method is also applicable to tissue specific pol II promoters. Likewise, the approach of Xia et al., (2002) *Nature Biotech.* 20:1006, avoids poly(A) tailing and can be used in connection with tissue-specific promoters.

Methods of generating RNAi include chemical synthesis, in vitro transcription, digestion of long dsRNA by Dicer (in vitro or in vivo), expression in vivo from a delivery vector, and expression in vivo from a PCR-derived RNAi expression cassette (see, e.g., TechNotes 10(3) "Five Ways to Produce siRNAs," from Ambion, Inc., Austin TX).

Guidelines for designing siRNA molecules are available (see e.g., literature from Ambion, Inc., Austin TX). In particular embodiments, the siRNA sequence has about 30-50% G/C content. Further, long stretches of greater than four T or A residues are generally avoided if RNA polymerase III is used to transcribe the RNA. Online siRNA target finders are available, e.g., from Ambion, Inc., through the Whitehead Institute of Biomedical Research, or from Dharmacon Research, Inc.

The antisense region of the RNAi molecule can be completely complementary to the target sequence, but need not be as long as it specifically hybridizes to the target sequence (as defined above) and reduces production of the protein product (e.g., by at least about 30%, 40%, 50%, 60%, 70%, 80%, 90%, 95% or more). In some embodiments, hybridization of such oligonucleotides to target sequences can be carried out under conditions of reduced stringency, medium stringency or even stringent conditions, as defined above.

In other embodiments, the antisense region of the RNAi has at least about 60%, 70%, 80%, 90%, 95%, 97%, 98% or higher sequence identity with the complement of the target sequence and reduces production of the protein product (e.g., by at least about 30%, 40%, 50%, 60%, 70%, 80%, 90%, 95% or more). In some embodiments, the antisense region contains 1, 2, 3, 4, 5, 6, 7, 8, 9 or 10 mismatches as compared with the target sequence. Mismatches are generally tolerated better at the ends of the dsRNA than in the center portion.

In particular embodiments, the RNAi is formed by intermolecular complexing between two separate sense and antisense molecules. The RNAi comprises a ds region formed by the intermolecular basepairing between the two separate strands. In other embodiments, the RNAi comprises a ds region formed by intramolecular basepairing within a single nucleic acid molecule comprising both sense and antisense regions, typically as an inverted repeat (e.g., a shRNA or other stem loop structure, or a circular RNAi molecule). The RNAi can further comprise a spacer region between the sense and antisense regions.

Generally, RNAi molecules are highly selective. If desired, those skilled in the art can readily eliminate candidate RNAi that are likely to interfere with expression of nucleic acids other than the target by searching relevant databases to identify RNAi sequences that do not have substantial sequence homology with other known sequences, for example, using BLAST (available at www.ncbi.nlm.nih.gov/BLAST).

Kits for the production of RNAi are commercially available, e.g., from New England Biolabs, Inc. and Ambion, Inc.

The recombinant virus vector may also comprise a heterologous nucleotide sequence that shares homology with and recombines with a locus on the host chromosome. This approach may be utilized to correct a genetic defect in the host cell.

The present invention also provides recombinant virus vectors that express an immunogenic polypeptide, e.g., for vaccination. The heterologous nucleic acid may encode any immunogen of interest known in the art including, but are not limited to, immunogens from human immunodeficiency virus, influenza virus, gag proteins, tumor antigens, cancer antigens, bacterial antigens, viral antigens, and the like. Alternatively, the immunogen can be presented in the virus capsid (e.g., incorporated therein) or tethered to the virus capsid (e.g., by covalent modification).

The use of parvoviruses as vaccines is known in the art (see, e.g., Miyamura et al., (1994) *Proc. Nat. Acad Sci. USA* 91:8507; U.S. Pat. No. 5,916,563 to Young et al., U.S. Pat. No. 5,905,040 to Mazzara et al., U.S. Pat. Nos. 5,882,652, 5,863,541 to Samulski et al.; the disclosures of which are incorporated herein in their entireties by reference). The antigen may be presented in the virus capsid. Alternatively, the antigen may be expressed from a heterologous nucleic acid introduced into a recombinant vector genome.

An immunogenic polypeptide, or immunogen, may be any polypeptide suitable for protecting the subject against a disease, including but not limited to microbial, bacterial, protozoal, parasitic, fungal and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen may also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia, such as the vaccinia L1 or L8 genes), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen, or a severe acute respiratory syndrome (SARS) immunogen such as a S [S1 or S2], M, E, or N protein or an immunogenic fragment thereof). The immunogen may further be a polio immunogen, herpes immunogen (e.g., CMV, EBV, HSV immunogens) mumps immunogen, measles immunogen, rubella immunogen, diphtheria toxin or other diphtheria immunogen, pertussis antigen, hepatitis (e.g., hepatitis A, hepatitis B or hepatitis C) immunogen, or any other vaccine immunogen known in the art.

Alternatively, the immunogen may be any tumor or cancer cell antigen. Optionally, the tumor or cancer antigen is expressed on the surface of the cancer cell. Exemplary cancer and tumor cell antigens are described in S. A. Rosenberg, (1999) *Immunity* 10:281). Illustrative cancer and tumor antigens include, but are not limited to: BRCA1 gene product, BRCA2 gene product, gp100, tyrosinase, GAGE-1/2, BAGE, RAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J Exp. Med.,* 180:347; Kawakami et al., (1994) *Cancer Res.* 54:3124) including MART-1 (Coulie et al., (1991) 1 Exp. Med. 180:35), gp100 (Wick et al., (1988)*J Cutan. Pathol.*

4:201) and MAGE antigen (MAGE-1, MAGE-2 and MAGE-3) (Van der Bruggen et al., (1991) *Science,* 254: 1643), CEA, TRP-1; TRP-2; β-15 and tyrosinase (Brichard et al., (1993) *J Exp. Med.* 178:489); HER-2/neu gene product (U.S. Pat. No. 4,968,603); CA 125; HE4; LK26; FB5 (endosialin); TAG 72; AFP; CA19-9; NSE; DU-PAN-2; CA50; Span-1; CA72-4; HCG; STN (sialyl Tn antigen); c-erbB-2 proteins; PSA; L-CanAg; estrogen receptor; milk fat globulin; p53 tumor suppressor protein (Levine, (1993) *Ann. Rev. Biochem.* 62:623); mucin antigens (international patent publication WO 90/05142); telomerases; nuclear matrix proteins; prostatic acid phosphatase; papilloma virus antigens; and antigens associated with the following cancers: melanomas, adenocarcinoma, thymoma, sarcoma, lung cancer, liver cancer, colorectal cancer, non-Hodgkin's lymphoma, Hodgkin's lymphoma, leukemias, uterine cancer, breast cancer, prostate cancer, ovarian cancer, cervical cancer, bladder cancer, kidney cancer, pancreatic cancer, brain cancer, kidney cancer, stomach cancer, esophageal cancer, head and neck cancer and others (see, e.g., Rosenberg, (1996) *Annu. Rev. Med.* 47:481-91).

Alternatively, the heterologous nucleotide sequence may encode any polypeptide that is desirably produced in a cell in vitro, ex vivo, or in vivo. For example, the virus vectors may be introduced into cultured cells and the expressed protein product isolated therefrom.

It will be understood by those skilled in the art that the heterologous nucleic acid(s) of interest may be operably associated with appropriate control sequences. For example, the heterologous nucleic acid may be operably associated with expression control elements, such as transcription/translation control signals, origins of replication, polyadenylation signals, internal ribosome entry sites (IRES), promoters, enhancers, and the like.

Those skilled in the art will further appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements can be native to the target cell or subject to be treated and/or native to the heterologous nucleic acid sequence. The promoter/enhancer element is generally chosen so that it will function in the target cell(s) of interest. In representative embodiments, the promoter/enhancer element is a mammalian promoter/enhancer element. The promoter/enhance element may be an RNA polymerase II-based promoter or an RNA polymerase III-based promoter. The promoter/enhance element may be constitutive or inducible.

Inducible expression control elements are generally used in those applications in which it is desirable to provide regulation over expression of the heterologous nucleic acid sequence(s). Inducible promoters/enhancer elements for gene delivery can be tissue-specific or tissue-preferred promoter/enhancer elements, and include muscle specific or preferred (including cardiac, skeletal and/or smooth muscle), neural tissue specific or preferred (including brain-specific), eye (including retina-specific and cornea-specific), liver specific or preferred, bone marrow specific or preferred, pancreatic specific or preferred, spleen specific or preferred, and lung specific or preferred promoter/enhancer elements. In one embodiment, a hepatocyte-specific or hepa-tocyte-preferred promoter is used. Examples of hepatocyte-specific or preferred promoters include, without limitation, apolipoprotein AII, albumin, alpha 1-antitrypsin, thyroxine-binding globulin, cytochrome P450 CYP3A4, or microRNA122 or a synthetic liver-specific regulatory sequence. Use of a hepatocyte-specific or preferred promoter can increase the specificity achieved by the synthetic AAV vector by further limiting expression of the heterologous nucleic acid to the liver. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally employed for efficient translation of inserted protein coding sequences. These exogenous translational control sequences, which may include the ATG initiation codon and adjacent sequences, can be of a variety of origins, both natural and synthetic.

The invention also provides synthetic AAV particles comprising an AAV capsid and an AAV genome, wherein the AAV genome "corresponds to" (i.e., encodes) the AAV capsid. Also provided are collections or libraries of such chimeric AAV particles, wherein the collection or library comprises 2 or more, 10 or more, 50 or more, 100 or more, 1000 or more, $10^4$ or more, $10^5$ or more, or $10^6$ or more distinct sequences.

The present invention further encompasses "empty" capsid particles (i.e., in the absence of a vector genome) comprising, consisting of, or consisting essentially of the synthetic AAV capsid proteins of the invention. The synthetic AAV capsids of the invention can be used as "capsid vehicles," as has been described in U.S. Pat. No. 5,863,541. Molecules that can be covalently linked, bound to or packaged by the virus capsids and transferred into a cell include DNA, RNA, a lipid, a carbohydrate, a polypeptide, a small organic molecule, or combinations of the same. Further, molecules can be associated with (e.g., "tethered to") the outside of the virus capsid for transfer of the molecules into host target cells. In one embodiment of the invention the molecule is covalently linked (i.e., conjugated or chemically coupled) to the capsid proteins. Methods of covalently linking molecules are known by those skilled in the art.

The virus capsids of the invention also find use in raising antibodies against the novel capsid structures. As a further alternative, an exogenous amino acid sequence may be inserted into the virus capsid for antigen presentation to a cell, e.g., for administration to a subject to produce an immune response to the exogenous amino acid sequence.

The invention also provides nucleic acids (e.g., isolated nucleic acids) encoding the synthetic virus capsids and synthetic capsid proteins of the invention. Further provided are vectors comprising the nucleic acids, and cells (in vivo or in culture) comprising the nucleic acids and/or vectors of the invention. Such nucleic acids, vectors and cells can be used, for example, as reagents (e.g., helper constructs or packaging cells) for the production of virus vectors as described herein.

In exemplary embodiments, the invention provides nucleic acid sequences encoding the AAV capsid of SEQ ID NOS: 4-6 or at least 90% identical to the nucleotide sequence of SEQ ID NOS: 1-3. The invention also provides nucleic acids encoding the AAV capsid variants, capsid protein variants and fusion proteins as described above. In particular embodiments, the nucleic acid hybridizes to the complement of the nucleic acid sequences specifically disclosed herein under standard conditions as known by those skilled in the art and encodes a variant capsid and/or capsid protein. Optionally, the variant capsid or capsid protein substantially retains at least one property of the capsid and/or capsid or capsid protein encoded by the nucleic acid sequence of SEQ ID NOS: 1-3. For example, a virus particle comprising the variant capsid or variant capsid protein can substantially retain the liver tropism profile of a virus particle comprising a capsid or capsid protein encoded by a nucleic acid coding sequence of SEQ ID NO: 1-3.

For example, hybridization of such sequences may be carried out under conditions of reduced stringency, medium stringency or even stringent conditions. Exemplary conditions for reduced, medium and stringent hybridization are as follows: (e.g., conditions represented by a wash stringency of 35-40% Formamide with 5×Denhardt's solution, 0.5% SDS and 1×SSPE at 37° C.; conditions represented by a wash stringency of 40-45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C., respectively). See, e.g., Sambrook et al., *Molecular Cloning, A Laboratory Manual* (2d Ed. 1989) (Cold Spring Harbor Laboratory).

In other embodiments, nucleic acid sequences encoding a variant capsid or capsid protein of the invention have at least about 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%, or higher sequence identity with the nucleic acid sequence of SEQ ID NO: 1-3 and optionally encode a variant capsid or capsid protein that substantially retains at least one property of the capsid or capsid protein encoded by a nucleic acid of SEQ ID NO: 1-3.

As is known in the art, a number of different programs can be used to identify whether a nucleic acid or polypeptide has sequence identity to a known sequence. Percent identity as used herein means that a nucleic acid or fragment thereof shares a specified percent identity to another nucleic acid, when optimally aligned (with appropriate nucleotide insertions or deletions) with the other nucleic acid (or its complementary strand), using BLASTN. To determine percent identity between two different nucleic acids, the percent identity is to be determined using the BLASTN program "BLAST 2 sequences". This program is available for public use from the National Center for Biotechnology Information (NCBI) over the Internet (Altschul et al., (1997) *Nucleic Acids Res.* 25(17):3389-3402). The parameters to be used are whatever combination of the following yields the highest calculated percent identity (as calculated below) with the default parameters shown in parentheses: Program-blastn Matrix-0 BLOSUM62 Reward for a match-0 or 1 (1) Penalty for a mismatch-0, -1, -2 or -3 (-2) Open gap penalty-0, 1, 2, 3, 4 or 5 (5) Extension gap penalty-0 or 1 (1) Gap x_dropoff-0 or 50 (50) Expect-10.

Percent identity or similarity when referring to polypeptides, indicates that the polypeptide in question exhibits a specified percent identity or similarity when compared with another protein or a portion thereof over the common lengths as determined using BLASTP. This program is also available for public use from the National Center for Biotechnology Information (NCBI) over the Internet (Altschul et al., 1997) *Nucleic Acids Res.* 25(17):3389-3402). Percent identity or similarity for polypeptides is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

In particular embodiments, the nucleic acid can comprise, consist essentially of, or consist of a vector including but not limited to a plasmid, phage, viral vector (e.g., AAV vector, an adenovirus vector, a herpesvirus vector, or a baculovirus vector), bacterial artificial chromosome (BAC), or yeast artificial chromosome (YAC). For example, the nucleic acid can comprise, consist of, or consist essentially of an AAV vector comprising a 5' and/or 3' terminal repeat (e.g., 5' and/or 3' AAV terminal repeat).

In some embodiments, the nucleic acid encoding the synthetic AAV capsid protein further comprises an AAV rep coding sequence. For example, the nucleic acid can be a helper construct for producing viral stocks.

The invention also provides packaging cells stably comprising a nucleic acid of the invention. For example, the nucleic acid can be stably incorporated into the genome of the cell or can be stably maintained in an episomal form (e.g., an "EBV based nuclear episome").

The nucleic acid can be incorporated into a delivery vector, such as a viral delivery vector. To illustrate, the nucleic acid of the invention can be packaged in an AAV particle, an adenovirus particle, a herpesvirus particle, a baculovirus particle, or any other suitable virus particle.

Moreover, the nucleic acid can be operably associated with a promoter element. Promoter elements are described in more detail herein.

The present invention further provides methods of producing the virus vectors of the invention. In a representative embodiment, the present invention provides a method of producing a recombinant virus vector, the method comprising providing to a cell in vitro, (a) a template comprising (i) a heterologous nucleic acid, and (ii) packaging signal sequences sufficient for the encapsidation of the AAV template into virus particles (e.g., one or more (e.g., two) terminal repeats, such as AAV terminal repeats), and (b) AAV sequences sufficient for replication and encapsidation of the template into viral particles (e.g., the AAV rep and AAV cap sequences encoding an AAV capsid of the invention). The template and AAV replication and capsid sequences are provided under conditions such that recombinant virus particles comprising the template packaged within the capsid are produced in the cell. The method can further comprise the step of collecting the virus particles from the cell. Virus particles may be collected from the medium and/or by lysing the cells.

In one illustrative embodiment, the invention provides a method of producing a rAAV particle comprising an AAV capsid, the method comprising: providing a cell in vitro with a nucleic acid encoding a synthetic AAV capsid of the invention, an AAV rep coding sequence, an AAV vector genome comprising a heterologous nucleic acid, and helper functions for generating a productive AAV infection; and allowing assembly of the AAV particles comprising the AAV capsid and encapsidating the AAV vector genome.

The cell is typically a cell that is permissive for AAV viral replication. Any suitable cell known in the art may be employed, such as mammalian cells. Also suitable are trans-complementing packaging cell lines that provide functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an EBV based nuclear episome.

As a further alternative, the rep/cap sequences may be stably carried (episomal or integrated) within a cell.

Typically, the AAV rep/cap sequences will not be flanked by the AAV packaging sequences (e.g., AAV ITRs), to prevent rescue and/or packaging of these sequences.

The template (e.g., an rAAV vector genome) can be provided to the cell using any method known in the art. For example, the template may be supplied by a non-viral (e.g., plasmid) or viral vector. In particular embodiments, the template is supplied by a herpesvirus or adenovirus vector (e.g., inserted into the E1a or E3 regions of a deleted adenovirus). As another illustration, Palombo et al., (1998) *J Virol.* 72:5025, describe a baculovirus vector carrying a reporter gene flanked by the AAV ITRs. EBV vectors may also be employed to deliver the template, as described above with respect to the rep/cap genes.

In another representative embodiment, the template is provided by a replicating rAAV virus. In still other embodiments, an AAV provirus is stably integrated into the chromosome of the cell.

To obtain maximal virus titers, helper virus functions (e.g., adenovirus or herpesvirus) essential for a productive AAV infection are generally provided to the cell. Helper virus sequences necessary for AAV replication are known in the art. Typically, these sequences are provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes required for efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper genes integrated in the chromosome or maintained as a stable extrachromosomal element. In representative embodiments, the helper virus sequences cannot be packaged into AAV virions, e.g., are not flanked by AAV ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct, but is optionally a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further contains the rAAV template. The AAV rep/cap sequences and/or the rAAV template may be inserted into a deleted region (e.g., the E1a or E3 regions) of the adenovirus.

In a further embodiment, the AAV rep/cap sequences and the adenovirus helper sequences are supplied by a single adenovirus helper vector. The rAAV template is provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as a "EBV based nuclear episome," see Margolski, (1992) *Curr. Top. Microbiol. Immun.* 158:67).

In a further exemplary embodiment, the AAV rep/cap sequences and adenovirus helper sequences are provided by a single adenovirus helper. The rAAV template is provided as a separate replicating viral vector. For example, the rAAV template may be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, in representative embodiments, the adenovirus helper sequences and the AAV rep/cap sequences are not flanked by the AAV packaging sequences (e.g., the AAV ITRs), so that these sequences are not packaged into the AAV virions.

Herpesvirus may also be used as a helper virus in AAV packaging methods. Hybrid herpesviruses encoding the AAV rep protein(s) may advantageously facilitate for more scalable AAV vector production schemes. A hybrid herpes simplex virus type I (HSV-1) vector expressing the AAV-2 rep and cap genes has been described (Conway et al., (1999) *Gene Therapy* 6:986 and WO 00/17377, the disclosures of which are incorporated herein in their entireties).

As a further alternative, the virus vectors of the invention can be produced in insect cells using baculovirus vectors to deliver the rep/cap genes and rAAV template as described by Urabe et al., (2002) *Human Gene Therapy* 13:1935-43.

Other methods of producing AAV use stably transformed packaging cells (see, e.g., U.S. Pat. No. 5,658,785).

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al., (1999) *Gene Therapy* 6:973). In representative embodiments, deleted replication-defective helper viruses are used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

The inventive packaging methods may be employed to produce high titer stocks of virus particles. In particular embodiments, the virus stock has a titer of at least about $10^5$ transducing units (tu)/ml, at least about $10^6$ tu/ml, at least about $10^7$ tu/ml, at least about $10^8$ tu/ml, at least about $10^9$ tu/ml, or at least about $10^{10}$ tu/ml.

The novel capsid protein and capsid structures find use in raising antibodies, for example, for diagnostic or therapeutic uses or as a research reagent. Thus, the invention also provides antibodies against the novel capsid proteins and capsids of the invention.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep or human, or can be a chimeric antibody. See, e.g., Walker et al., *Mol. Immunol.* 26, 403-11 (1989). The antibodies can be recombinant monoclonal antibodies, for example, produced according to the methods disclosed in U.S. Pat. No. 4,474,893 or U.S. Pat. No. 4,816,567. The antibodies can also be chemically constructed, for example, according to the method disclosed in U.S. Pat. No. 4,676,980.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254, 1275-1281).

Polyclonal antibodies can be produced by immunizing a suitable animal (e.g., rabbit, goat, etc.) with an antigen to which a monoclonal antibody to the target binds, collecting immune serum from the animal, and separating the polyclonal antibodies from the immune serum, in accordance with known procedures.

Monoclonal antibodies can be produced in a hybridoma cell line according to the technique of Kohler and Milstein, (1975) *Nature* 265, 495-97. For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in *E. coli* by recombinant techniques known to those skilled in the art. See, e.g., W. Huse, (1989) *Science* 246, 1275-81.

Antibodies specific to a target polypeptide can also be obtained by phage display techniques known in the art.

Various immunoassays can be used for screening to identify antibodies having the desired specificity. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). A two-site, monoclonal-based immunoassay utilizing monoclonal antibodies reactive to two non-interfering epitopes can be used as well as a competitive binding assay.

Antibodies can be conjugated to a solid support (e.g., beads, plates, slides or wells formed from materials such as latex or polystyrene) in accordance with known techniques. Antibodies can likewise be directly or indirectly conjugated to detectable groups such as radiolabels (e.g., $^{35}$S, $^{125}$I, $^{131}$I), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art.

III. Methods of Using Synthetic AAV Capsids

The present invention also relates to methods for delivering heterologous nucleotide sequences into the liver while minimizing delivery to other organs. The virus vectors of the invention may be employed to deliver a nucleotide sequence of interest to a hepatocyte in vitro, e.g., to produce a polypeptide or nucleic acid in vitro or for ex vivo gene therapy. The vectors are additionally useful in a method of delivering a nucleotide sequence to a subject in need thereof, e.g., to express a therapeutic or immunogenic polypeptide or nucleic acid. In this manner, the polypeptide or nucleic acid may thus be produced in vivo in the subject. The subject may be in need of the polypeptide or nucleic acid because the subject has a deficiency of the polypeptide, or because the production of the polypeptide or nucleic acid in the subject may impart some therapeutic effect, as a method of treatment or otherwise, and as explained further below.

In particular embodiments, the vectors are useful to express a polypeptide or nucleic acid that provides a beneficial effect to the subject in general. In other embodiments, the vectors are useful to express a polypeptide or nucleic acid that provides a beneficial effect to cells in the liver (e.g., hepatocytes).

Thus, one aspect of the invention relates to a method of delivering a nucleic acid of interest to a hepatocyte, the method comprising contacting the hepatocyte with the AAV particle of the invention.

In another aspect, the invention relates to a method of delivering a nucleic acid of interest to a hepatocyte in a mammalian subject, the method comprising administering an effective amount of the AAV particle or pharmaceutical formulation of the invention to a mammalian subject, thereby delivering the nucleic acid of interest to a hepatocyte in the mammalian subject.

A further aspect of the invention relates to a method of treating a disorder in a mammalian subject in need thereof, wherein the disorder is treatable by expressing a product in the liver of the subject, the method comprising administering a therapeutically effective amount of the AAV particle of the invention to the subject, wherein the product is expressed, thereby treating the disorder.

In general, the virus vectors of the invention may be employed to deliver any foreign nucleic acid with a biological effect to treat or ameliorate the symptoms associated with any disorder related to gene expression. Further, the invention can be used to treat any disease state for which it is beneficial to deliver a therapeutic polypeptide. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (inhibitory RNA including without limitation RNAi such as siRNA or shRNA, antisense RNA or microRNA to remove repeats), amyotrophic lateral sclerosis, epilepsy (galanin, neurotrophic factors), and other neurological disorders, cancer (endostatin, angiostatin, TRAIL, FAS-ligand, cytokines including interferons; inhibitory RNA including without limitation RNAi (such as siRNA or shRNA), antisense RNA and microRNA including inhibitory RNA against VEGF, the multiple drug resistance gene product or a cancer immunogen), diabetes mellitus (insulin, PGC-α1, GLP-1, myostatin pro-peptide, glucose transporter 4), muscular dystrophies including Duchenne and Becker (e.g., dystrophin, mini-dystrophin, micro-dystrophin, insulin-like growth factor I, a sarcoglycan [e.g., α, β, γ], Inhibitory RNA [e.g., RNAi, antisense RNA or microRNA] against myostatin or myostatin propeptide, laminin-alpha2, Fukutin-related protein, dominant negative myostatin, follistatin, activin type II soluble receptor, anti-inflammatory polypeptides such as the Ikappa B dominant mutant, sarcospan, utrophin, mini-utrophin, inhibitory RNA [e.g., RNAi, antisense RNA or microRNA] against splice junctions in the dystrophin gene to induce exon skipping [see, e.g., WO/2003/095647], inhibitory RNA (e.g., RNAi, antisense RNA or micro RNA] against U7 snRNAs to induce exon skipping [see, e.g., WO/2006/021724], and antibodies or antibody fragments against myostatin or myostatin propeptide), Gaucher disease (glucocerebrosidase), Hurler's disease (α-L-iduronidase), adenosine deaminase deficiency (adenosine deaminase), glycogen storage diseases (e.g., Fabry disease [α-galactosidase]and Pompe disease [lysosomal acid α-glucosidase]) and other metabolic defects including other lysosomal storage disorders and glycogen storage disorders, congenital emphysema (al-antitrypsin), Lesch-Nyhan Syndrome (hypoxanthine guanine phosphoribosyl transferase), Niemann-Pick disease (sphingomyelinase), Maple Syrup Urine Disease (branched-chain keto acid dehydrogenase), retinal degenerative diseases (and other diseases of the eye and retina; e.g., PDGF, endostatin and/or angiostatin for macular degeneration), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver (RNAi such as siRNA or shRNA, microRNA or antisense RNA for hepatitis B and/or hepatitis C genes), kidney, heart including congestive heart failure or peripheral artery disease (PAD) (e.g., by delivering protein phosphatase inhibitor I [I-1], phospholamban, sarcoplasmic endoreticulum $Ca^{2+}$-ATPase [serca2a], zinc finger proteins that regulate the phospholamban gene, Pim-1, PGC-1α, SOD-1, SOD-2, ECF-SOD, kallikrein, thymosin-β4, hypoxia-inducible transcription factor [HIF], βarkct, β2-adrenergic receptor, β2-adrenergic receptor kinase [βARK], phosphoinositide-3 kinase [PI3 kinase], calsarcin, an angiogenic factor, S100A1, parvalbumin, adenylyl cyclase type 6, a molecule that effects G-protein coupled receptor kinase type 2 knockdown such as a truncated constitutively active bARKct, an inhibitory RNA [e.g., RNAi, antisense RNA or microRNA] against phospholamban; phospholamban inhibitory or dominant-negative molecules such as phospholamban S16E, etc.), arthritis (insulin-like growth factors), joint disorders (insulin-like growth factors), intimal hyperplasia (e.g., by delivering enos, inos), improve survival of heart transplants (superoxide dismutase), AIDS (soluble CD4), muscle wasting (insulin-like growth factor I, myostatin pro-peptide, an anti-apoptotic factor, follistatin), limb ischemia (VEGF, FGF, PGC-1α, EC-SOD, HIF), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including RANKL and/or VEGF) can be administered with a bone allograft, for example, following a break or surgical removal in a cancer patient.

Exemplary lysosomal storage diseases that can be treated according to the present invention include without limitation: Hurler's Syndrome (MPS IH), Scheie's Syndrome (MPS IS), and Hurler-Scheie Syndrome (MPS IH/S) (α-L-iduronidase); Hunter's Syndrome (MPS II) (iduronate sulfate sulfatase); Sanfilippo A Syndrome (MPS IIIA) (Heparan-S-sulfate sulfaminidase), Sanfilippo B Syndrome (MPS IIIB) (N-acetyl-D-glucosaminidase), Sanfilippo C Syndrome (MPS IIIC) (Acetyl-CoA-glucosaminide N-acetyl-transferase), Sanfilippo D Syndrome (MPS IIID) (N-acetyl-glucosaminine-6-sulfate sulfatase); Morquio A disease (MPS IVA) (Galactosamine-6-sulfate sulfatase), Morquio B disease (MPS IV B) (β-Galactosidase); Maroteaux-lmay disease (MPS VI) (arylsulfatase B); Sly Syndrome (MPS VII) (0-glucuronidase); hyaluronidase deficiency (MPS IX) (hyaluronidase); sialidosis (mucolipidosis I), mucolipidosis II (I-Cell disease) (N-actylglucos-aminyl-1-phosphotransferase catalytic subunit), mucolipidosis III (pseudo-Hurler polydystrophy) (N-acetylglucos-aminyl-1-phosphotransferase; type IIIA [catalytic subunit] and type IIIC [substrate recognition subunit]); GM1 gangliosidosis (ganglioside β-galactosidase), GM2 gangliosidosis Type I (Tay-Sachs disease) (β-hexaminidase A), GM2 gangliosidosis type II (Sandhoff's disease) (β-hexosaminidase B); Niemann-Pick disease (Types A and B) (sphingomyelinase); Gaucher's disease (glucocerebrosidase); Farber's disease (ceraminidase); Fabry's disease (α-galactosidase A); Krabbe's disease (galactosylceramide β-galactosidase); metachromatic leukodystrophy (arylsulfatase A); lysosomal acid lipase deficiency including Wolman's disease (lysosomal acid lipase); Batten disease (juvenile neuronal ceroid lipofuscinosis) (lysosomal trans-membrane CLN3 protein) sialidosis (neuraminidase 1); galactosialidosis (Goldberg's syndrome) (protective protein/cathepsin A); α-mannosidosis (α-D-mannosidase); β-mannosidosis (β-D-mannosidosis); fucosidosis (α-D-fucosidase); aspartylglucosaminuria (N-Aspartylglucosaminidase); and sialuria (Na phosphate cotransporter).

Exemplary glycogen storage diseases that can be treated according to the present invention include, but are not limited to, Type Ia GSD (von Gierke disease) (glucose-6-phosphatase), Type Ib GSD (glucose-6-phosphate translocase), Type Ic GSD (microsomal phosphate or pyrophosphate transporter), Type Id GSD (microsomal glucose transporter), Type II GSD including Pompe disease or infantile Type IIa GSD (lysosomal acid α-glucosidase) and Type IIb (Danon) (lysosomal membrane protein-2), Type IIIa and IIIb GSD (Debrancher enzyme; amyloglucosidase and oligoglucanotransferase), Type IV GSD (Andersen's disease) (branching enzyme), Type V GSD (McArdle disease) (muscle phosphorylase), Type VI GSD (Hers' disease) (liver phosphorylase), Type VII GSD (Tarui's disease) (phosphofructokinase), GSD Type VIII/IXa (X-linked phosphorylase kinase), GSD Type IXb (Liver and muscle phosphorylase kinase), GSD Type IXc (liver phosphorylase kinase), GSD Type IXd (muscle phosphorylase kinase), GSD O (glycogen synthase), Fanconi-Bickel syndrome (glucose transporter-2), phosphoglucoisomerase deficiency, muscle phosphoglycerate kinase deficiency, phosphoglycerate mutase deficiency, fructose 1,6-diphosphatase deficiency, phosphoenolpyruvate carboxykinase deficiency, and lactate dehydrogenase deficiency.

Gene transfer has substantial potential use in understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using inhibitory RNA such as RNAi (e.g., siRNA or shRNA), microRNA or antisense RNA. For unbalanced disease states, gene transfer can be used to create a disease state in a model system, which can then be used in efforts to counteract the disease state. Thus, the virus vectors according to the present invention permit the treatment of genetic diseases. As used herein, a disease state is treated by partially or wholly remedying the deficiency or imbalance that causes the disease or makes it more severe. The use of site-specific recombination of nucleic sequences to cause mutations or to correct defects is also possible.

The virus vectors according to the present invention may also be employed to provide an antisense nucleic acid or inhibitory RNA (e.g., microRNA or RNAi such as a siRNA or shRNA) to a cell in vitro or in vivo. Expression of the inhibitory RNA in the target cell diminishes expression of a particular protein(s) by the cell. Accordingly, inhibitory RNA may be administered to decrease expression of a particular protein in a subject in need thereof. Inhibitory RNA may also be administered to cells in vitro to regulate cell physiology, e.g., to optimize cell or tissue culture systems.

As a further aspect, the virus vectors of the present invention may be used to produce an immune response in a subject. According to this embodiment, a virus vector comprising a nucleic acid encoding an immunogen may be administered to a subject, and an active immune response (optionally, a protective immune response) is mounted by the subject against the immunogen. Immunogens are as described hereinabove.

Alternatively, the virus vector may be administered to a cell ex vivo and the altered cell is administered to the subject. The heterologous nucleic acid is introduced into the cell, and the cell is administered to the subject, where the heterologous nucleic acid encoding the immunogen is optionally expressed and induces an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment of disease, in particular cancer or tumors (e.g., by causing regression of a cancer or tumor and/or by preventing metastasis and/or by preventing growth of metastatic nodules). The protective effects may be complete or partial, as long as the benefits of the treatment outweigh any disadvantages thereof.

The virus vectors of the present invention may also be administered for cancer immunotherapy by administration of a viral vector expressing a cancer cell antigen (or an immunologically similar molecule) or any other immunogen that produces an immune response against a cancer cell. To illustrate, an immune response may be produced against a cancer cell antigen in a subject by administering a viral vector comprising a heterologous nucleotide sequence encoding the cancer cell antigen, for example to treat a patient with cancer. The virus vector may be administered to a subject in vivo or by using ex vivo methods, as described herein.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to, leukemia, lymphoma (e.g., Hodgkin and non-Hodgkin lymphomas), colorectal cancer, renal cancer, liver cancer, breast cancer, lung cancer, prostate cancer, testicular cancer, ovarian cancer, uterine cancer, cervical cancer, brain cancer (e.g., gliomas and glioblastoma), bone cancer, sarcoma, melanoma, head and neck cancer, esophageal cancer, thyroid cancer, and the like. In embodiments of the invention, the invention is practiced to treat and/or prevent tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

Cancer cell antigens have been described hereinabove. By the terms "treating cancer" or "treatment of cancer," it is intended that the severity of the cancer is reduced or the cancer is prevented or at least partially eliminated. For example, in particular contexts, these terms indicate that metastasis of the cancer is prevented or reduced or at least partially eliminated. In further representative embodiments these terms indicate that growth of metastatic nodules (e.g., after surgical removal of a primary tumor) is prevented or reduced or at least partially eliminated. By the terms "prevention of cancer" or "preventing cancer" it is intended that the methods at least partially eliminate or reduce the incidence or onset of cancer. Alternatively stated, the onset or progression of cancer in the subject may be slowed, controlled, decreased in likelihood or probability, or delayed.

In particular embodiments, cells may be removed from a subject with cancer and contacted with a virus vector according to the present invention. The modified cell is then administered to the subject, whereby an immune response against the cancer cell antigen is elicited. This method is particularly advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (e.g., CTL inductive cytokines) may be administered to a subject in conjunction with the virus vectors.

Cytokines may be administered by any method known in the art. Exogenous cytokines may be administered to the subject, or alternatively, a nucleotide sequence encoding a cytokine may be delivered to the subject using a suitable vector, and the cytokine produced in vivo.

The viral vectors are further useful for targeting liver cells for research purposes, e.g., for study of liver function in vitro or in animals or for use in creating and/or studying animal models of disease. For example, the vectors can be used to deliver heterologous nucleic acids to hepatocytes in animal models of liver injury, e.g., fibrosis or cirrhosis or animal models of liver diseases such as viral infections (e.g., hepatitis viruses).

Further, the virus vectors according to the present invention find further use in diagnostic and screening methods, whereby a gene of interest is transiently or stably expressed in a cell culture system, or alternatively, a transgenic animal model. The invention can also be practiced to deliver a nucleic acid for the purposes of protein production, e.g., for laboratory, industrial or commercial purposes.

Recombinant virus vectors according to the present invention find use in both veterinary and medical applications. Suitable subjects include both avians and mammals. The term "avian" as used herein includes, but is not limited to, chickens, ducks, geese, quail, turkeys, pheasant, parrots, parakeets. The term "mammal" as used herein includes, but is not limited to, humans, primates non-human primates (e.g., monkeys and baboons), cattle, sheep, goats, pigs, horses, cats, dogs, rabbits, rodents (e.g., rats, mice, hamsters, and the like), etc. Human subjects include neonates, infants, juveniles, and adults. Optionally, the subject is "in need of" the methods of the present invention, e.g., because the subject has or is believed at risk for a disorder including those described herein or that would benefit from the delivery of a nucleic acid including those described herein. As a further option, the subject can be a laboratory animal and/or an animal model of disease.

In particular embodiments, the present invention provides a pharmaceutical composition comprising a virus vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleotide sequence to a cell in vitro. The virus vector may be introduced to the cells at the appropriate multiplicity of infection according to standard transduction methods appropriate for the particular target cells. Titers of the virus vector or capsid to administer can vary, depending upon the target cell type and number, and the particular virus vector or capsid, and can be determined by those of skill in the art without undue experimentation. In particular embodiments, at least about $10^3$ infectious units, more preferably at least about $10^5$ infectious units are introduced to the cell.

The cell(s) into which the virus vector can be introduced may be of any type, including but not limited to neural cells (including cells of the peripheral and central nervous systems, in particular, brain cells such as neurons, oligodendrocytes, glial cells, astrocytes), lung cells, cells of the eye (including retinal cells, retinal pigment epithelium, and corneal cells), epithelial cells (e.g., gut and respiratory epithelial cells), skeletal muscle cells (including myoblasts, myotubes and myofibers), diaphragm muscle cells, dendritic cells, pancreatic cells (including islet cells), hepatic cells, a cell of the gastrointestinal tract (including smooth muscle cells, epithelial cells), heart cells (including cardiomyocytes), bone cells (e.g., bone marrow stem cells), hematopoietic stem cells, spleen cells, keratinocytes, fibroblasts, endothelial cells, prostate cells, joint cells (including, e.g., cartilage, meniscus, synovium and bone marrow), germ cells, and the like. Alternatively, the cell may be any progenitor cell. As a further alternative, the cell can be a stem cell (e.g., neural stem cell, liver stem cell). As still a further alternative, the cell may be a cancer or tumor cell (cancers and tumors are described above). Moreover, the cells can be from any species of origin, as indicated above.

The virus vectors may be introduced to cells in vitro for the purpose of administering the modified cell to a subject. In particular embodiments, the cells have been removed from a subject, the virus vector is introduced therein, and the cells are then replaced back into the subject. Methods of removing cells from subject for treatment ex vivo, followed by introduction back into the subject are known in the art (see, e.g., U.S. Pat. No. 5,399,346). Alternatively, the recombinant virus vector is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ or about $10^3$ to about $10^6$ cells will be administered per dose in a pharmaceutically acceptable carrier. In particular embodiments, the cells transduced with the virus vector are administered to the subject in an effective amount in combination with a pharmaceutical carrier.

In some embodiments, cells that have been transduced with the virus vector may be administered to elicit an immunogenic response against the delivered polypeptide (e.g., expressed as a transgene or in the capsid). Typically, a quantity of cells expressing an effective amount of the polypeptide in combination with a pharmaceutically acceptable carrier is administered. Optionally, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vectors or capsids of the invention to subjects. In particular embodiments, the method comprises a method of delivering a nucleic acid of interest to an animal subject, the method comprising: administering an effective amount of a virus vector according to the invention to an animal subject. Administration of the virus vectors of the present invention to a human subject or an animal in need thereof can be by any means known in the art. Optionally, the virus vector is delivered in an effective dose in a pharmaceutically acceptable carrier.

The virus vectors of the invention can further be administered to a subject to elicit an immunogenic response (e.g., as a vaccine). Typically, vaccines of the present invention comprise an effective amount of virus in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vectors to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$ transducing units or more, preferably about $10^7$ or $10^8$, $10^9$, $10^{10}$, $10^{11}$, $10^{12}$, $10^{13}$, $10^{14}$ or $10^{15}$ transducing units, yet more preferably about $10^{12}$ to $10^{14}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intro-lymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and on the nature of the particular vector that is being used.

In some embodiments, the viral vector is administered directly to the liver. Direct administration can result in high specificity of transduction of hepatocytes, e.g., wherein at least 80%, 85%, 90%, 95% or more of the transduced cells are hepatocytes. Any method known in the art to administer vectors directly to the liver can be used. The vector may be introduced by direct injection into the liver or injection into an artery or vein feeding the liver, e.g., intraportal delivery.

Typically, the viral vector will be administered in a liquid formulation by systemic delivery or direct injection to the desired region or compartment in the liver. In some embodiments, the vector can be delivered via a reservoir and/or pump. In other embodiments, the vector may be provided by topical application to the desired region or by intra-nasal administration of an aerosol formulation. Administration to the eye or into the ear, may be by topical application of liquid droplets. As a further alternative, the vector may be administered as a solid, slow-release formulation. Controlled release of parvovirus and AAV vectors is described by international patent publication WO 01/91803.

Delivery to any of these tissues can also be achieved by delivering a depot comprising the virus vector, which can be implanted into the tissue or the tissue can be contacted with a film or other matrix comprising the virus vector. Examples of such implantable matrices or substrates are described in U.S. Pat. No. 7,201,898).

Injectables can be prepared in conventional forms, either as liquid solutions or suspensions, solid forms suitable for solution or suspension in liquid prior to injection, or as emulsions. Alternatively, one may administer the virus vector in a local rather than systemic manner, for example, in a depot or sustained-release formulation. Further, the virus vector can be delivered dried to a surgically implantable matrix such as a bone graft substitute, a suture, a stent, and the like (e.g., as described in U.S. Pat. No. 7,201,898).

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a virus vector of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, Pharm. Res. 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The virus vectors disclosed herein may be administered to the lungs of a subject by any suitable means, for example, by administering an aerosol suspension of respirable particles comprised of the virus vectors, which the subject inhales. The respirable particles may be liquid or solid. Aerosols of liquid particles comprising the virus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors may likewise be produced with any solid particulate medicament aerosol generator, by techniques known in the pharmaceutical art.

Having described the present invention, the same will be explained in greater detail in the following examples, which are included herein for illustration purposes only, and which are not intended to be limiting to the invention.

Example 1

Construction of AAV Capsid Gene Shuffled Library

The construction of a AAV capsid gene shuffled library was as described before (Yang et al., *Proc. Natd. Acad. Sci. USA* $10^6$(10):3946 (2009); Yang et al., *Meth. Mol. Biol.* 709:127 (2011)) Capsid genes of AAV serotypes 1, 2, 3B, 4, 6, 7, 8, and 9 were cloned into the same vector pXX-UF1-AAV containing AAV2 inverted terminal repeats (ITRs) and AAV2 Rep gene. These plasmids containing ITRs, AAV2 Rep and each of the eight different Cap genes were named pXX-UF1-AAVn sequentially. The capsid genes were amplified by the primers CAP-5' 5'-CCC-AAGCTTCGAT-CAACTACGCAGACAGGTACCAA-3' (SEQ ID NO:7) and CAP-3' 5'-ATAAGAAT-GCGGCCGC-AGAGAC-CAAAGTTCAACTGAAACGA-3' (SEQ ID NO:8), mixed in the same ratio for DNA shuffling (Stemmer, *Proc. Natl. Acad. Sci. USA* 91:10747 (1994)). In brief, 4 μg of the DNA templates were treated with 0.04 U of DNase I at 15° C. briefly and 300-500 and 500-1000 bp fragments were purified from the agarose gel for reassembly of capsid genes using pfu DNA polymerase. The reassembled capsid genes were re-amplified by pfu DNA polymerase using CAP5'/CAP3' primers, digested with HindIII/NotI, and ligated into HindIII/NotI-digested pXX-UF1-AAV vector that contained AAV2 ITRs flanking AAV2 Rep and Cap genes. The HindIII/Not I digestion effectively removed the AAV2 capsid gene for the replacement of the PCR amplified fragments of the liver-enriched Cap genes. The PCR program was 94° C. for 5 min; 94° C. for 1 min, 75° C. for 5 min for hot start, 60° C. for 1 min, 72° C. for 4.5 min; 29 cycles of 94° C. for 1 min, 60° C. for 1 min, 72° C. for 4.5 min; 72° C. for 10 min. The reconstructed plasmids were transformed into *E. coli* DH10B cells and a number of clones were randomly picked for restriction enzyme analysis to determine the recombination frequency and packaging viability. The resultant ITR-containing infectious AAV plasmid library was used to produce a self-packaging AAV viral particle library.

Example 2

In Vivo Enrichment in Mouse Liver

For in vivo screening of AAV variants targeting to the liver, $1\times10^{11}$ vg (vector genomes)/mouse of the chimeric AAV library were administered into adult C57BL/6J mice via tail vein. Two weeks later, mouse tissues including liver and other tissues were collected for genomic DNA isolation using phenol/chloroform extraction. After PCR amplification of the total liver DNA using the common primers for the capsid genes, the PCR products were recloned into the AAV plasmid backbone containing the AAV2 ITRs and the Rep gene. Thus, the capsid gene PCR products and the pXX-UF1-AAV vector were both digested with HindIII/NotI and ligated for cloning. The second round production of infectious AAV particles was generated from the first round in vivo enrichment and injected in mice again. This in vivo enrichment process was repeated in mice for three times.

The final PCR product of the highly enriched capsid genes was cloned in a universal precursor of AAV packaging plasmid that contained the AAV2 Rep gene without the AAV inverted terminal repeats (ITRs). The capsid genes were ligated downstream of the Rep gene and upstream of the AAV polyadenylation signal sequence to reconstitute the Rep and Cap gene expression cassettes. The ligation products were electroporated into E. coli strain DH10B and grown on Amp resistant plates. Individual colonies were picked and miniprep DNA isolated for DNA sequencing of the capsid genes. A number of novel capsid genes were found and two of them were highly enriched. These two capsid genes were named AAVXL32 and AAVXL12. Their DNA sequences are shown in SEQ ID NOS:1 and 2 and amino acid sequences are shown in SEQ ID NOS:4 and 5. While AAVXL12 and AAVXL32 DNA sequences differ by 23 nucleotides (23 out of 2214 nucleotides), their amino acid sequences differ only by 2 residues (2 out of 737 amino acids). Amino acid 220 is S in XL12 and D in XL32; and amino acid 643 is N in XL12 and H in XL32.

Example 3

Production of AAV Vectors Containing Reporter Genes

The capsid-specific packaging plasmids were produced by the conventional large scale preparation method and purified by CsCl density ultracentrifugation twice. These plasmids were used for packaging of AAV vectors containing reporter genes such as green fluorescent protein GFP and beta-galactosidase Lac-Z genes under the transcriptional control of ubiquitous promoters CMV or CB (CMV-enhancer plus chicken beta-actin basal promoter). The AAV vectors were packaged in each novel capsid and purified by the conventional double CsCl density ultracentrifugation. The titers of the reporter vectors were determined by DNA dot blot method against known copy numbers of the corresponding reporter vector plasmid DNA. All vector yields were in the normal range.

Example 4

In Vivo Examination of Liver Enriched AAV Capsids in Mice

To examine if the in vivo enriched and selected novel capsids are potent in transducing the liver, AAVXL12 and AAVXL32 were used to separately package two reporter genes, GFP and LacZ. The vectors were purified, titered and intravenously injected via the tail vein of C57B/6 mice at a dose of $5 \times 10^2$ vg/kg body weight. AAV9 vectors packaging the same GFP and LacZ genes were used as a positive control as AAV9 gene transfer is robust in mouse liver. As shown in FIGS. 1A-1B, the results revealed that for both GFP and LacZ reporter genes, AAVXL12 and AAVXL32 achieved essentially the same levels of liver gene expression as the control AAV9, confirming the in vivo selection strategy that enriched liver-tropic capsid genes in mouse.

Example 5

In Vitro Examination of Liver Enriched AAV Capsids on Human Liver Cancer Cell Line To see if the liver-tropic capsids are able to transduce liver cells of human origin, the vectors were first examined in vitro on a human liver cancer cell line named Huh7. Huh7 is widely used for in vitro assays for AAV vector gene expression with liver-specific promoters. The cell line retains some of the features of human hepatocytes and shows a positive correlation with cultured primary human hepatocytes. Therefore, this cell line can be used for initial testing of the liver tropism of AAV capsids for cells of human origin. Again, AAV9 was used as a positive control. As shown in FIG. 2, both AAVXL12 and AAVXL32 achieved highly efficient gene expression at a multiplicity of infections (moi) of $1 \times 10^5$ vg/cell and $1 \times 10^4$ vg/cell. On the other hand, AAV9 was not efficient in transducing the Huh7 cells. Only a few lacZ positive cells were detected at the higher moi. These results suggest that AAVXL12 and AAVXL32 could possess high affinity to human liver cells in addition to mouse liver cells.

Example 6

In Vitro Examination of Liver Enriched AAV Capsids on Human and Dog Primary Hepatocytes Because certain AAV serotypes transduce mouse liver extremely well but poorly transduce human or non-human (monkey) liver (Hurlbut et al., Mol. Ther.18:1983 (2010)), whereas other serotypes poorly transduce mouse liver but perform very well in a mouse model of humanized liver (Lisowski et al., Nature 506(7488):382 (2014)) and monkeys (Li et al., Mol. Ther. 12:1867 (2015)), this discrepancy prompted an examination of whether the novel liver-tropic AAV capsids also effectively transduce human as well as canine primary hepatocytes culture.

The vectors were first examined in vitro on human primary hepatocytes isolated from three human donors. The hepatocytes were purchased from TRL (Triangle Research Laboratories, currently an Invitrogen subsidiary) and cultured with media provided by the vendor and according to their protocols. GFP under the control of ubiquitous CMV promoter was used as the reporter gene and packaged in AAVXL12, AAVXL32, and AAV2, 6, 7, 8, 9, etc. These vectors were used to infect the primary hepatocyte culture at about 80% cell confluence and a vector dose at a moi of $1 \times 10^5$ vg/cell. Fluorescent photographs were taken at different time points on the cells for GFP expression that displayed green color. As shown in FIGS. 3A-3D, the results revealed that whereas the widely reported serotype capsids such as AAV8 and AAV9 robustly transduced the mouse liver, these vectors displayed very poor infectivity on primary human hepatocytes. By contract, the novel liver-tropic AAV capsids enriched in mouse liver also transduced primary human hepatocytes at the highest efficiencies amongst all other naturally occurring vectors tested in this study. At 24 hours post infection (FIG. 3A), other serotypes of AAV barely had any GFP expression whereas AAVXL12 and AAVXL32 already had significant GFP expression. At 48 hours post infection (FIG. 3B), AAVXL12 and AAVXL32 again showed the highest level of GFP expression. Hepatocytes infected with the above 2 vectors were continued in culture for 7 days and GFP photographs were taken on a daily basis. The intensity of GFP fluorescence increases with time and reached the highest level at day 7 (FIGS. 3C and 3D). Thus, the novel capsids are in distinct contrast to other AAV capsids such as AAV3 and AAVLK03 (Lisowski et al., Nature 506(7488):382 (2014)) and monkeys (Li et al., Mol. Ther. 12:1867 (2015)) that very poorly transduce mouse liver but robustly transduce human hepatocytes in the humanized mouse liver as well as non-human primate liver. Other AAV serotypes such as AAV2 and AAV5 are reported to poorly transduce both mouse and non-human primate livers. The above finding strongly suggested that both AAVXL12 and AAVXL32 possess unique properties that are not seen in other known AAV capsids.

Figure 4B:
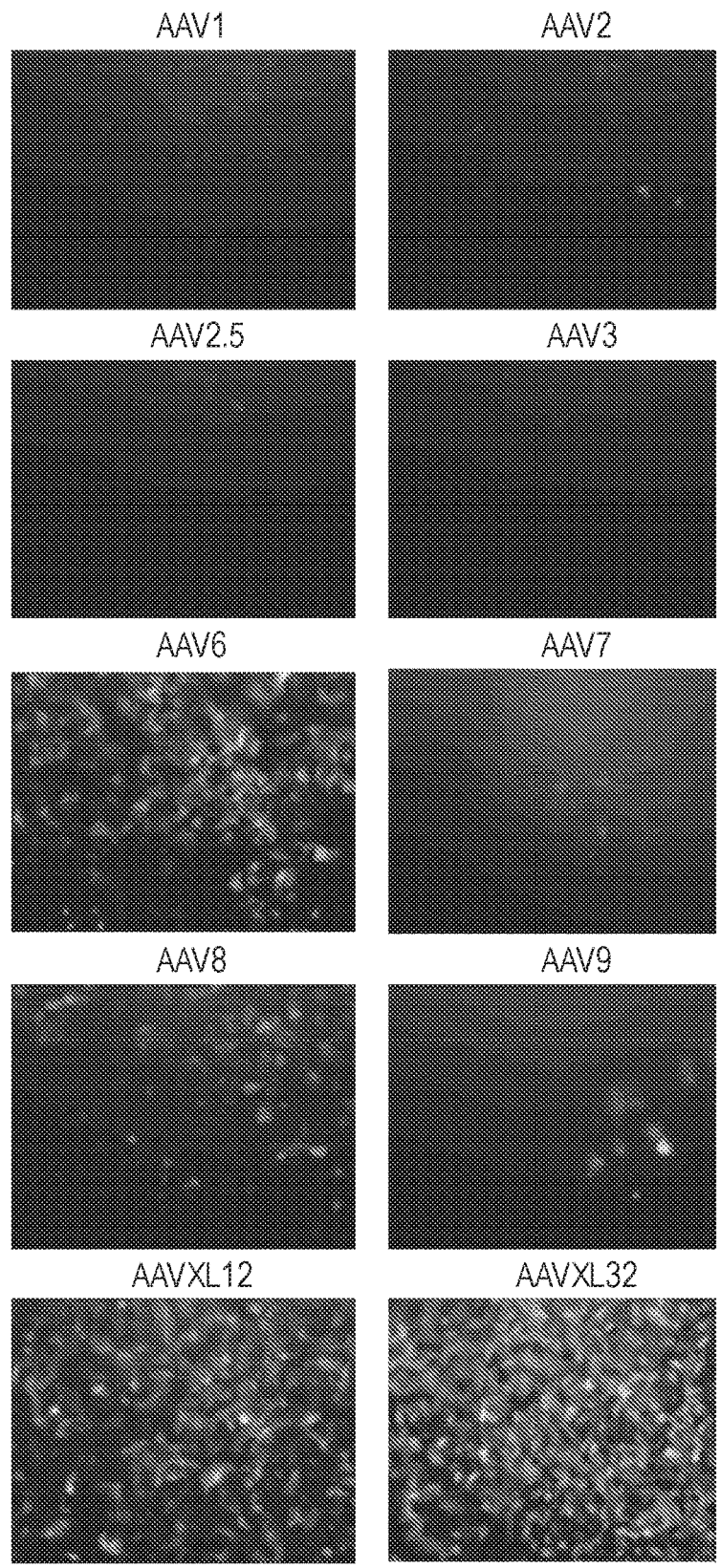
Figure 4C:
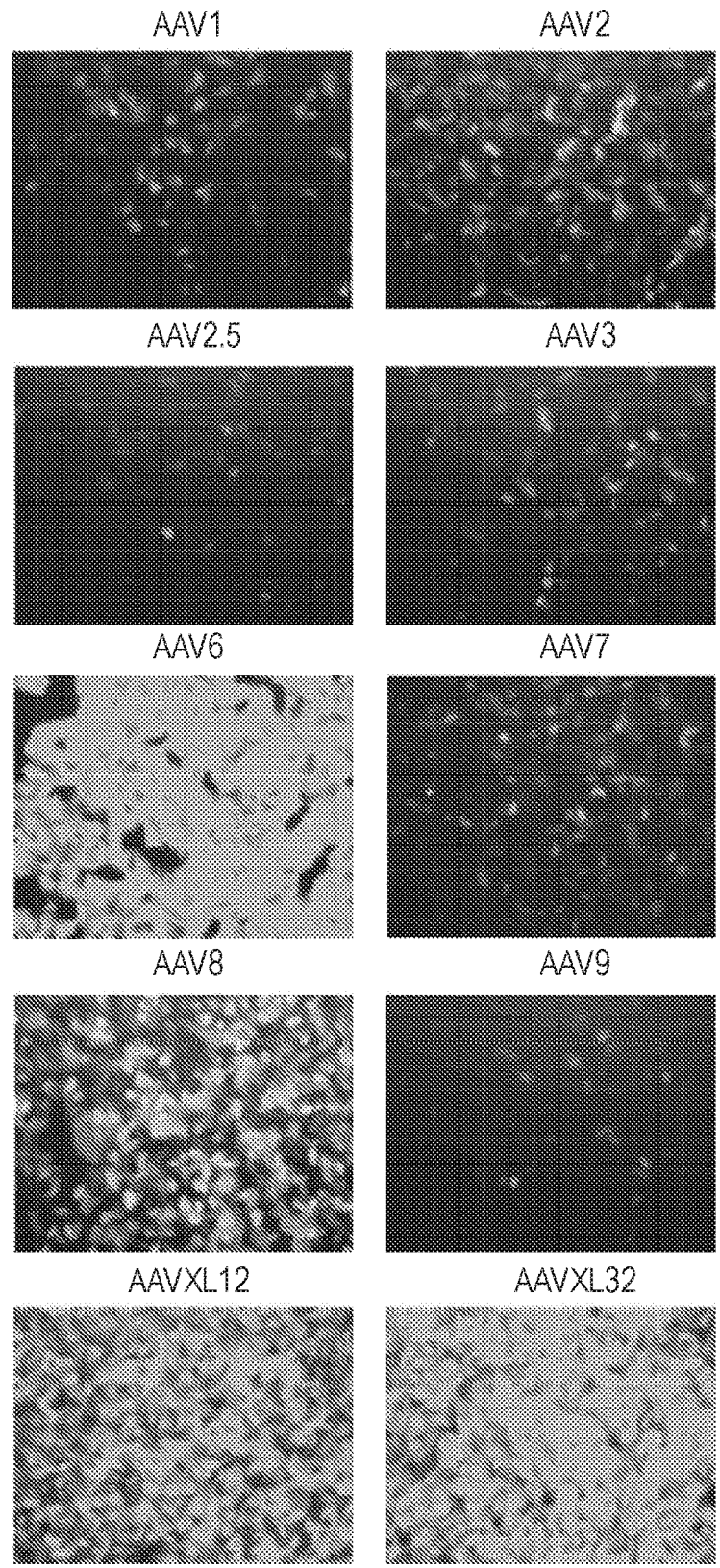

Subsequently, dog primary hepatocytes were also used to examine the infectivity of the liver-tropic AAV and compare with a number of commonly used AAV capsids containing GFP reporter gene. The AAV vector genome particles were used at a mo. of $1 \times 10^5$ vg/cell. Cryopreserved and fresh hepatocytes from two dogs were used. At 24 and 48 hours post infection, green fluorescence photographs were taken on AAV GFP vector infected cells. As shown in FIGS. 4A-4C, AAVXL12 and AAVXL32 displayed higher gene transfer efficiency than other serotypes tested except AAV6, which is similar or slightly higher than AAVXL12 and AAVXL32. Notably, although AAV6 showed high level gene transfer in dog hepatocytes, this was not observed in human primary hepatocyte culture. These results demonstrate that AAVXL12 and AAVXL32 both had high infectivities on canine hepatocytes.

Example 7

In Vivo Examination of AAVXL32 in Non-Human Primate Liver

Next it was examined whether the liver-tropic capsids are also able to achieve efficient gene transfer in non-human primate livers. AAVXL32 was chosen to compare with AAV8. The latter has been previously reported to be able to transduce monkey livers and also been used in liver-directed gene therapy in humans for hemophilia B clinical trials. Adult male Rhesus Macaque monkeys of 3-5 years of age were screened for serum neutralizing antibodies against AAVXL32 and AAV8 according to previously published papers. Four monkeys with neutralizing antibody titers lower than 1:8 were chosen to be injected intravenously with AAV vectors. Two monkeys were injected with AAVXL32-CB-GFP and two injected with AAV-CB-GFP at a dose of $1 \times 10^1$ vg/kg body weight. The AAV vector expression cassette was in a double-stranded (also called self-complementary) form for faster and more efficient gene expression. Two weeks later the monkeys were euthanized and liver tissues were taken for cryo-thin-sections and green fluorescent photography. As shown in FIG. 5, AAVXL32 achieved significantly higher levels of GFP expression than AAV8 in the monkey livers. GFP positive cells are readily detected with higher fluorescent intensity and more positive cells (as pointed out by arrows) in the AAVXL32 treated monkeys. On the other hand, AAV8 treated monkeys showed much fewer positive cells and weaker fluorescent intensity. These results strongly suggest that AAVXL32 is significantly more liver-tropic than AAV8 in non-human primates.

Example 8

Figure 6:
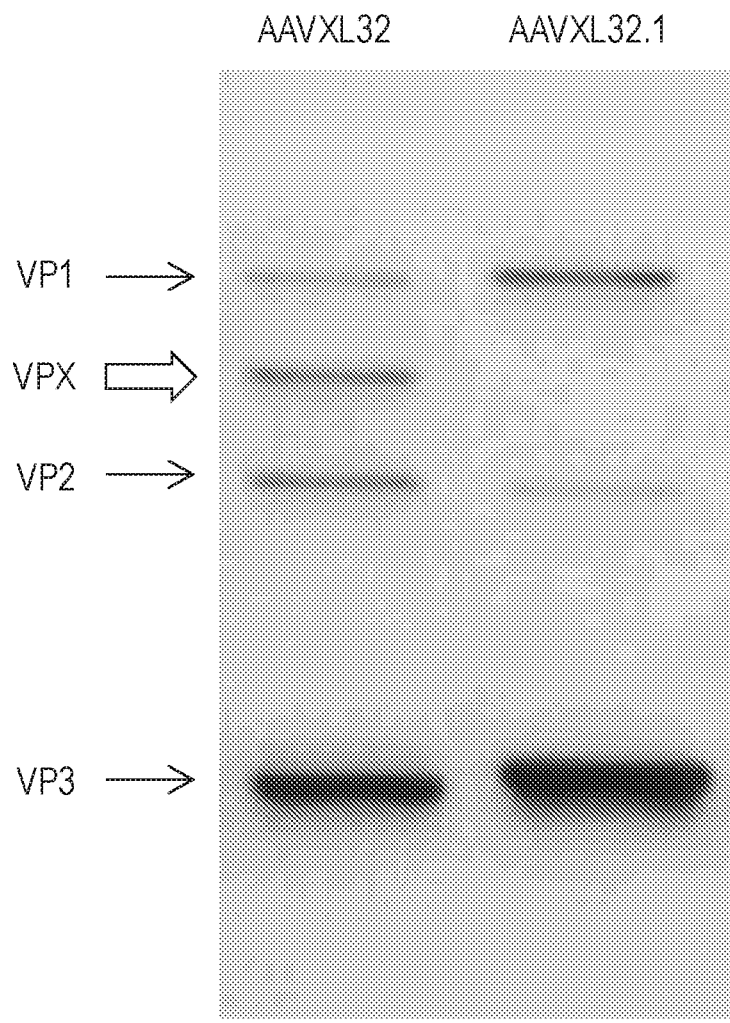
FIG. 6 shows the protein gel analysis of AAVXL32 and AAVXL32.1 capsids. Highly purified AAVXL32 and AAVXL32.1 were loaded at a concentration of $1 \times 10^{11}$ particles per lane and analyzed on SDS-PAGE gel and visualized by silver staining. Arrows highlight the typical AAV capsid proteins VP1, VP2 and VP3. Arrowhead highlights the extra capsid protein VPX in AAVXL32, possibly resulting from a weaker start codon generated by a CTC to CTG mutation. Reversion of the CTG to CTC abolished this protein in AAVXL32.1.

Characterization of AAVXL32 Capsid Proteins and Removal of a Weak Start Codon for a Third Capsid Protein To characterize the capsid protein, double CsCl ultracentrifugation purified and DNA dot blot titered AAVXL32 capsid was analyzed. The purified vectors were loaded onto a SDS PAGE gel to determine the molecule weight of the VP proteins after silver staining. As shown in FIG. 6, the AAVXL32 displayed 4 bands. In addition to the typical VP1, VP2, and VP3 proteins of all natural AAVs, there was an extra band (herein named VPX) between VP1 and VP2. This extra band was a result of a single nucleotide site-directed mutagenesis of AAV7 and AAV8 capsid genes at the XhoI restriction site located in the large protein VP1 unique region. The original purpose of making this mutation was for the convenience of DNA cloning in the AAV capsid genes DNA shuffling library, which included capsid genes of AAV serotypes 1, 2, 3, 4, 6, 7, 8 and 9 (Yang et al., Proc. Natl. Acad. Sci. USA $10^6(10):3946$ (2009)). The single C to G mutation at the XhoI site (CTCGAG to CTGGAG) at nucleotide 219 counting from the VP1 start codon created a sense mutation for the amino acid leucine in both AAV7 and AAV8 capsid genes. It did not alter the VP1 protein amino acid sequence. However, it was suspected this sense mutation created a weaker non-consensus start codon CTG (vs. the classic ATG start codon). This could have led to the generation of the extra capsid protein VPX between VP1 and VP2. Apparently this extra band did not compromise the vector DNA packaging and infectivity in a discernible manner. In order to confirm that the sense mutation created a weak start codon for the extra capsid protein, a site-directed mutagenesis was performed to reverse the C to G mutation back to the original C of wildtype AAV7 and AAV8 sequences. The new capsid gene with the revertant mutation, named AAVXL32.1, indeed inactivated the weak start codon and removed the extra capsid band between VP1 and VP2 (FIG. 6). The LacZ reporter gene vector packaged in either XL32 or XL32.1 did not show apparent differences in vector yield and infectivity, suggesting that the extra capsid band played an insignificant or unknown role in AAV capsid functions.

Example 9

Prevalence of Neutralization Antibodies in Human Sera Samples

Pre-existing neutralizing antibody (Nab) against AAV capsids in the human population is a significant problem for AAV-mediated in vivo gene therapy. Some serotypes of AAV such as AAV2 and AAV3 have a very high prevalence of Nabs (Ling, J. Integr. Med. 5:341 (2015)). A preliminary assessment on the prevalence of Nab against the liver-tropic AAVXL32 capsid was performed. The prevalence of Nab in the sera samples of a group of Chinese patients was examined with their identities complete blinded. Specifically, sera from 100 different persons were tested for their preexisting NAb against AAVXL32 capsids. The Nab assay was essentially done according to previous published methods by Ling et al and references there in (Ling, J. Integr. Med. 5:341 (2015)). A modification was made by using a secreted luciferase (Gaussia luciferase) as the reporter gene and a human liver cell line Huh7 as the tester cells. Briefly, $5 \times 10^4$ cells/well of Huh7 cells were plated in round bottom 96-well plate. The next day, individual serum samples were serially diluted with a 2-fold increment. The Nab positive control was pooled sera from AAVXL32 immunized mice and the negative control was pooled naive mouse sera purchased from Sigma. The diluted serum samples and the AAV were incubated at 37° C. for 1 hour and added to the plate that had been seeded with Huh7 cells one day earlier. At 48 hours post AAVXL32 infection, a small aliquot of the cell culture media were taken from each well for luciferase activity assay. Unlike the firefly luciferase, *Gaussia* luciferase is a secreted enzyme and there is no need to lyse the cells for the enzyme activity measurement. The results showed that more than 50% of the serum samples had a Nab titer lower than 1:8 dilution and approximately 70% at lower than 1:16 dilution. These data indicate that the Nab prevalence of AAVXL32 was much lower than previously published data on AAV2, AAV3, AAVKL3, AAV5 and AAV8 in the Chinese population. In those studies, AAV2, AAV3 and AAVK03 were found to be neutralizing antibody positive in more than 90% of the subjects with a serum dilution cut off at 1:20 dilution, whereas AAV8 had a Nab positive rate above 80% and AAV5 above 70% at the same dilution cut off at 1:20.

The foregoing is illustrative of the present invention, and is not to be construed as limiting thereof. The invention is defined by the following claims, with equivalents of the claims to be included therein.

```
AAV Capsid Sequences
AAVXL12 capsid gene DNA sequence
                                                        SEQ ID NO: 1
ATGGCTGCCGATGGTTATCTTCCAGATTGGCTCGAGGACAACCTCTCTGAGGGCATTCGCGA

GTGGTGGGCGCTGAAACCTGGAGCCCCGAAGCCCAAAGCCAACCAGCAAAAGCAGGACGACG

GCCGGGGTCTGGTGCTTCCTGGCTACAAGTACCTCGGACCCTTCAACGGACTCGACAAGGGG

GAGCCCGTCAACGCGGCGGACGCAGCGGCCCTGGAGCACGACAAGGCCTACGACCAGCAGCT

GCAGGCGGGTGACAATCCGTACCTGCGGTATAACCACGCCGACGCCGAGTTTCAGGAGCGTC

TGCAAGAAGATACGTCTTTTGGGGCAACCTCGGGCGAGCAGTCTTCCAGGCCAAGAAGCGG

GTTCTCGAACCTCTCGGTCTGGTTGAGGAAGGCGCTAAGACGGCTCCTGGAAAGAAGAGACC

GGTAGAGCCATCACCCCAGCGTTCTCCAGACTCCTCTACGGGCATCGGCAAGAAAGGCCAAC

AGCCCGCCAGAAAAAGACTCAATTTTGGTCAGACTGGCGACTCAGAGTCAGTTCCAGACCCT

CAACCTCTCGGAGAACCTCCAGCAGCGCCCTCTGGTGTGGGACCTAATACAATGGCTTCAGG

CGGTGGCGCACCAATGGCAGACAATAACGAAGGCGCCTCCGGAGTGGGTAATGCCTCAGGAA

ATTGGCATTGCGATTCCACATGGCTGGGCGACAGAGTCATCACCACCAGCACCCGAACATGG

GCCTTGCCCACCTACAACAATCACCTCTACAAGCAAATCTCCAGTGCTTCAACGGGGGCCAG

CAACGACAACCACTACTTCGGCTACAGCACCCCCTGGGGGTATTTTGATTTCAACAGATTCC

ACTGCCACTTTTCACCACGTGACTGGCAGCGACTCATCAACAACAATTGGGGATTCCGGCCC

AAGAGACTCAACTTCAAACTCTTCAACATCCAAGTCAAGGAGGTCACGACGAATGATGGCGT

CACGACCATCGCTAATAACCTTACCAGCACGGTTCAAGTCTTCTCGGACTCGGAGTACCAGT

TGCCGTACGTCCTCGGCTCTGCGCACCAGGGCTGCCTCCCTCCGTTCCCGGCGGACGTGTTC

ATGATTCCGCAGTACGGCTACCTAACGCTCAACAATGGCAGCCAGGCAGTGGGACGGTCATC

CTTTTACTGCCTGGAATATTTCCCATCGCAGATGCTGAGAACGGGCAACAACTTTACCTTCA

GCTACACCTTTGAGGAAGTGCCTTTCCACAGCAGCTACGCGCACAGCCAGAGCCTGGACCGG

CTGATGAATCCTCTCATCGACCAATACCTGTATTACCTGAACAGAACTCAAAATCAGTCCGG

AAGTGCCCAAAACAAGGACTTGCTGTTTAGCCGTGGGTCTCCAGCTGGCATGTCTGTTCAGC

CCAAAAACTGGCTACCTGGACCCTGTTACCGGCAGCAGCGCGTTTCTAAAACAAAAACAGAC

AACAACAACAGCAACTTTACCTGGACTGGTGCTTCAAAATATAACCTTAATGGGCGTGAATC

TATAATCAACCCTGGCACTGCTATGGCCTCACACAAAGACGACAAAGACAAGTTCTTTCCCA

TGAGCGGTGTCATGATTTTTGGAAAGGAGAGCGCCGGAGCTTCAAACACTGCATTGGACAAT

GTCATGATCACAGACGAAGAGGAAATCAAAGCCACTAACCCCGTGGCCACCGAAAGATTTGG

GACTGTGGCAGTCAATCTCCAGAGCAGCAGCACAGACCCTGCGACCGGAGATGTGCATGTTA

TGGGAGCCTTACCTGGAATGGTGTGGCAAGACAGAGACGTATACCTGCAGGGTCCTATTTGG

GCCAAAATTCCTCACACGGATGGACACTTTCACCCGTCTCCTCTTATGGGCGGCTTTGGACT

CAAGAACCCGCCTCCTCAGATCCTCATCAAAAACACGCCTGTTCCTGCGAATCCTCCGGCAG

AGTTTTCGGCTACAAAGTTTGCTTCATTCATCACCCAGTATTCCACAGGACAAGTGAGCGTG
```

-continued

GAGATTGAATGGGAGCTGCAGAAAGAAAACAGCAAACGCTGGAATCCCGAAGTGCAGTATAC

ATCTAACTATGCAAAATCTGCCAACGTTGATTTCACTGTGGACAACAATGGACTTTATACTG

AGCCTCGCCCCATTGGCACCCGTTACCTCACCCGTCCCTGTAA

AAVXL32 capsid gene DNA sequence

SEQ ID NO: 2

ATGGCTGCCGATGGTTATCTTCCAGATTGGCTCGAGGACAACCTCTCTGAGGGCATTCGCGA

GTGGTGGGCGCTGAAACCTGGAGCCCCGAAGCCCAAAGCCAACCAGCAAAAGCAGGACGACG

GCCGGGGTCTGGTGCTTCCTGGCTACAAGTACCTCGGACCCTTCAACGGACTCGACAAGGGG

GAGCCCGTCAACGCGGCGGACGCAGCGGCCC<u>TGGAG</u>CACGACAAGGCCTACGACCAGCAGCT

GCAGGCGGGTGACAATCCGTACCTGCGGTATAACCACGCCGACGCCGAGTTTCAGGAGCGTC

TGCAAGAAGATACGTCTTTTGGGGGCAACCTCGGGCGAGCAGTCTTCCAGGCCAAGAAGCGG

GTTCTCGAACCTCTCGGTCTGGTTGAGGAAGGCGCTAAGACGGCTCCTGGAAAGAAGAGACC

GGTAGAGCCATCACCCCAGCGTTCTCCAGACTCCTCTACGGGCATCGGCAAGAAAGGCCAAC

AGCCCGCCAGAAAAAGACTCAATTTTGGTCAGACTGGCGACTCAGAGTCAGTTCCAGACCCT

CAACCTCTCGGAGAACCTCCAGCAGCGCCCTCTGGTGTGGGACCTAATACAATGGCTTCAGG

CGGTGGCGCACCAATGGCAGACAATAACGAAGGCGCCGACGGAGTGGGTAATGCCTCAGGAA

ATTGGCATTGCGATTCCACATGGCTGGGCGACAGAGTCATCACCACCAGCACCCGAACATGG

GCCTTGCCCACCTATAACAACCACCTCTACAAGCAAATCTCCAGTGCTTCAACGGGGCCAG

CAACGACAACCACTACTTCGGCTACAGCACCCCCTGGGGGTATTTTGATTTCAACAGATTCC

ACTGCCATTTCTCACCACGTGACTGGCAGCGACTCATCAACAACAATTGGGGATTCCGGCCC

AAGAGACTCAACTTCAAGCTCTTCAACATCCAAGTCAAGGAGGTCACGACGAATGATGGCGT

CACGACCATCGCTAATAACCTTACCAGCACGGTTCAAGTCTTCTCGGACTCGGAGTACCAGT

TGCCGTACGTCCTCGGCTCTGCGCACCAGGGCTGCCTCCCTCCGTTCCCGGCGGACGTGTTC

ATGATTCCGCAATACGGCTACCTGACGCTCAACAATGGCAGCCAAGCCGTGGGACGTTCATC

CTTTTACTGCCTGGAATATTTCCCTTCTCAGATGCTGAGAACGGGCAACAACTTTACCTTCA

GCTACACCTTTGAGGAAGTGCCTTTCCACAGCAGCTACGCGCACAGCCAGAGCCTGGACCGG

CTGATGAATCCTCTCATCGACCAGTACCTGTATTACCTGAACAGAACTCAGAATCAGTCCGG

AAGTGCCCAAAACAAGGACTTGCTGTTTAGCCGTGGGTCTCCAGCTGGCATGTCTGTTCAGC

CCAAAAACTGGCTACCTGGACCCTGTTACCGGCAGCAGCGCGTTTCTAAAACAAAAACAGAC

AACAACAACAGCAACTTTACCTGGACTGGTGCTTCAAAATATAACCTCAATGGGCGTGAATC

CATCATCAACCCTGGCACTGCTATGGCCTCACACAAAGACGACAAAGACAAGTTCTTTCCCA

TGAGCGGTGTCATGATTTTTGGAAAGGAGAGCGCCGGAGCTTCAAACACTGCATTGGACAAT

GTCATGATCACAGACGAAGAGGAAATCAAAGCCACTAACCCCGTGGCCACCGAAAGATTTGG

GACTGTGGCAGTCAATCTCCAGAGCAGCAGCACAGACCCTGCGACCGGAGATGTGCATGTTA

TGGGAGCCTTACCTGGAATGGTGTGGCAAGACAGAGACGTATACCTGCAGGGTCCTATTTGG

GCCAAAATTCCTCACACGGATGGACACTTTCACCCGTCTCCTCTCATGGGCGGCTTTGGACT

TAAGCACCCGCCTCCTCAGATCCTCATCAAAAACACGCCTGTTCCTGCGAATCCTCCGGCAG

AGTTTTCGGCTACAAAGTTTGCTTCATTCATCACCCAGTATTCCACAGGACAAGTGAGCGTG

GAGATTGAATGGGAGCTGCAGAAAGAAAACAGCAAACGCTGGAATCCCGAAGTGCAGTATAC

ATCTAACTATGCAAAATCTGCCAACGTTGATTTTACTGTGGACAACAATGGACTTTATACTG

AGCCTCGCCCCATTGGCACCCGTTACCTCACCCGTCCCTGTAA

-continued

AAVXL32.1 capsid gene DNA sequence

SEQ ID NO: 3

ATGGCTGCCGATGGTTATCTTCCAGATTGGCTCGAGGACAACCTCTCTGAGGGCATTCGCGA
GTGGTGGGCGCTGAAACCTGGAGCCCCGAAGCCCAAAGCCAACCAGCAAAAGCAGGACGACG
GCCGGGGTCTGGTGCTTCCTGGCTACAAGTACCTCGGACCCTTCAACGGACTCGACAAGGGG
GAGCCCGTCAACGCGGCGGACGCAGCGGCC<u>CTCGAG</u>CACGACAAGGCCTACGACCAGCAGCT
GCAGGCGGGTGACAATCCGTACCTGCGGTATAACCACGCCGACGCCGAGTTTCAGGAGCGTC
TGCAAGAAGATACGTCTTTTGGGGGCAACCTCGGGCGAGCAGTCTTCCAGGCCAAGAAGCGG
GTTCTCGAACCTCTCGGTCTGGTTGAGGAAGGCGCTAAGACGGCTCCTGGAAAGAAGAGACC
GGTAGAGCCATCACCCCAGCGTTCTCCAGACTCCTCTACGGGCATCGGCAAGAAAGGCCAAC
AGCCCGCCAGAAAAGACTCAATTTTGGTCAGACTGGCGACTCAGAGTCAGTTCCAGACCCT
CAACCTCTCGGAGAACCTCCAGCAGCGCCCTCTGGTGTGGGACCTAATACAATGGCTTCAGG
CGGTGGCGCACCAATGGCAGACAATAACGAAGGCGCCGACGGAGTGGGTAATGCCTCAGGAA
ATTGGCATTGCGATTCCACATGGCTGGGCGACAGAGTCATCACCACCAGCACCCGAACATGG
GCCTTGCCCACCTATAACAACCACCTCTACAAGCAAATCTCCAGTGCTTCAACGGGGGCCAG
CAACGACAACCACTACTTCGGCTACAGCACCCCCTGGGGGTATTTTGATTTCAACAGATTCC
ACTGCCATTTCTCACCACGTGACTGGCAGCGACTCATCAACAACAATTGGGGATTCCGGCCC
AAGAGACTCAACTTCAAGCTCTTCAACATCCAAGTCAAGGAGGTCACGACGAATGATGGCGT
CACGACCATCGCTAATAACCTTACCAGCACGGTTCAAGTCTTCTCGGACTCGGAGTACCAGT
TGCCGTACGTCCTCGGCTCTGCGCACCAGGGCTGCCTCCCTCCGTTCCCGGCGGACGTGTTC
ATGATTCCGCAATACGGCTACCTGACGCTCAACAATGGCAGCCAAGCCGTGGGACGTTCATC
CTTTTACTGCCTGGAATATTTCCCTTCTCAGATGCTGAGAACGGGCAACAACTTTACCTTCA
GCTACACCTTTGAGGAAGTGCCTTTCCACAGCAGCTACGCGCACAGCCAGAGCCTGGACCGG
CTGATGAATCCTCTCATCGACCAGTACCTGTATTACCTGAACAGAACTCAGAATCAGTCCGG
AAGTGCCCAAAACAAGGACTTGCTGTTTAGCCGTGGGTCTCCAGCTGGCATGTCTGTTCAGC
CCAAAAACTGGCTACCTGGACCCTGTTACCGGCAGCAGCGCGTTTCTAAAACAAAAACAGAC
AACAACAACAGCAACTTTACCTGGACTGGTGCTTCAAAATATAACCTCAATGGGCGTGAATC
CATCATCAACCCTGGCACTGCTATGGCCTCACACAAAGACGACAAAGACAAGTTCTTTCCCA
TGAGCGGTGTCATGATTTTTGGAAAGGAGAGCGCCGGAGCTTCAAACACTGCATTGGACAAT
GTCATGATCACAGACGAAGAGGAAATCAAAGCCACTAACCCCGTGGCCACCGAAAGATTTGG
GACTGTGGCAGTCAATCTCCAGAGCAGCAGCACAGACCCTGCGACCGGAGATGTGCATGTTA
TGGGAGCCTTACCTGGAATGGTGTGGCAAGACAGAGACGTATACCTGCAGGGTCCTATTTGG
GCCAAAATTCCTCACACGGATGGACACTTTCACCCGTCTCCTCTCATGGGCGGCTTTGGACT
TAAGCACCCGCCTCCTCAGATCCTCATCAAAAACACGCCTGTTCCTGCGAATCCTCCGGCAG
AGTTTTCGGCTACAAAGTTTGCTTCATTCATCACCCAGTATTCCACAGGACAAGTGAGCGTG
GAGATTGAATGGGAGCTGCAGAAAGAAAACAGCAAACGCTGGAATCCCGAAGTGCAGTATAC
ATCTAACTATGCAAAATCTGCCAACGTTGATTTTACTGTGGACAACAATGGACTTTATACTG
AGCCTCGCCCCATTGGCACCCGTTACCTCACCCGTCCCCTGTAA

AAVXL12 capsid amino acid sequence

SEQ ID NO: 4

MAADGYLPDWLEDNLSEGIREWWALKPGAPKPKANQQKQDDGRGLVLPGYKYLGPENGLD
KGEPVNAADAAALEHDKAYDQQLQAGDNPYLRYNHADAEFQERLQEDTSFGGNLGRAVEQ

AKKRVLEPLGLVEEGAKTAPGKKRPVEPSPQRSPDSSTGIGKKGQQPARKRLNFGQTGDS

ESVPDPQPLGEPPAAPSGVGPNTMASGGGAPMADNNEGASGVGNASGNWHCDSTWLGDRV

ITTSTRTWALPTYNNHLYKQISSASTGASNDNHYFGYSTPWGYFDFNRFHCHESPRDWQR

LINNNWGFRPKRLNFKLFNIQVKEVTTNDGVTTIANNLTSTVQVESDSEYQLPYVLGSAH

QGCLPPFPADVEMIPQYGYLTLNNGSQAVGRSSFYCLEYFPSQMLRTGNNFTFSYTFEEV

PFHSSYAHSQSLDRLMNPLIDQYLYYLNRTQNQSGSAQNKDLLFSRGSPAGMSVQPKNWL

PGPCYRQQRVSKTKTDNNNSNFTWTGASKYNLNGRESIINPGTAMASHKDDKDKFFPMSG

VMIFGKESAGASNTALDNVMITDEEEIKATNPVATERFGTVAVNLQSSSTDPATGDVHVM

GALPGMVWQDRDVYLQGPIWAKIPHTDGHFHPSPLMGGFGLKNPPPQILIKNTPVPANPP

AEFSATKFASFITQYSTGQVSVEIEWELQKENSKRWNPEVQYTSNYAKSANVDFTVDNNG

LYTEPRPIGTRYLTRPL

AAVXL32 capsid amino acid sequence
                                                      SEQ ID NO: 5
MAADGYLPDWLEDNLSEGIREWWALKPGAPKPKANQQKQDDGRGLVLPGYKYLGPENGLD

KGEPVNAADAAALEHDKAYDQQLQAGDNPYLRYNHADAEFQERLQEDTSFGGNLGRAVEQ

AKKRVLEPLGLVEEGAKTAPGKKRPVEPSPQRSPDSSTGIGKKGQQPARKRLNFGQTGDS

ESVPDPQPLGEPPAAPSGVGPNTMASGGGAPMADNNEGADGVGNASGNWHCDSTWLGDRV

ITTSTRTWALPTYNNHLYKQISSASTGASNDNHYFGYSTPWGYFDENRFHCHFSPRDWQR

LINNNWGFRPKRLNFKLFNIQVKEVTTNDGVTTIANNLTSTVQVFSDSEYQLPYVLGSAH

QGCLPPFPADVFMIPQYGYLTLNNGSQAVGRSSFYCLEYFPSQMLRTGNNFTFSYTFEEV

PFHSSYAHSQSLDRLMNPLIDQYLYYLNRTQNQSGSAQNKDLLFSRGSPAGMSVQPKNWL

PGPCYRQQRVSKTKTDNNNSNFTWTGASKYNLNGRESIINPGTAMASHKDDKDKFFPMSG

VMIFGKESAGASNTALDNVMITDEEEIKATNPVATERFGTVAVNLQSSSTDPATGDVHVM

GALPGMVWQDRDVYLQGPIWAKIPHTDGHFHPSPLMGGFGLKHPPPQILIKNTPVPANPP

AEFSATKFASFITQYSTGQVSVEIEWELQKENSKRWNPEVQYTSNYAKSANVDFTVDNNG

LYTEPRPIGTRYLTRPL

AAV XL32.1 capsid amino acid sequence
                                                      SEQ ID NO: 6
MAADGYLPDWLEDNLSEGIREWWALKPGAPKPKANQQKQDDGRGLVLPGYKYLGPENGLD

KGEPVNAADAAALEHDKAYDQQLQAGDNPYLRYNHADAEFQERLQEDTSFGGNLGRAVFQ

AKKRVLEPLGLVEEGAKTAPGKKRPVEPSPQRSPDSSTGIGKKGQQPARKRLNFGQTGDS

ESVPDPQPLGEPPAAPSGVGPNTMASGGGAPMADNNEGADGVGNASGNWHCDSTWLGDRV

ITTSTRTWALPTYNNHLYKQISSASTGASNDNHYFGYSTPWGYFDFNRFHCHESPRDWQR

LINNNWGFRPKRLNFKLFNIQVKEVTTNDGVTTIANNLTSTVQVFSDSEYQLPYVLGSAH

QGCLPPFPADVFMIPQYGYLTLNNGSQAVGRSSFYCLEYFPSQMLRTGNNFTFSYTFEEV

PFHSSYAHSQSLDRLMNPLIDQYLYYLNRTQNQSGSAQNKDLLFSRGSPAGMSVQPKNWL

PGPCYRQQRVSKTKTDNNNSNFTWTGASKYNLNGRESIINPGTAMASHKDDKDKFFPMSG

VMIFGKESAGASNTALDNVMITDEEEIKATNPVATERFGTVAVNLQSSSTDPATGDVHVM

GALPGMVWQDRDVYLQGPIWAKIPHTDGHFHPSPLMGGFGLKHPPPQILIKNTPVPANPP

AEFSATKFASFITQYSTGQVSVEIEWELQKENSKRWNPEVQYTSNYAKSANVDFTVDNNG

LYTEPRPIGTRYLTRPL

-continued

DNA Primer CAP-5'
SEQ ID NO: 7
5'-CCC-AAGCTTCGATCAACTACGCAGACAGGTACCAA-3'

DNA Primer CAP-3'
SEQ ID NO: 8
5'-ATAAGAAT-GCGGCCGC-AGAGACCAAAGTTCAACTGAAACGA-3'

---

We claim:

1. A nucleic acid comprising an adeno-associated virus (AAV) capsid protein coding sequence, which encodes SEQ ID NO:5.

2. The nucleic acid of claim 1, wherein the AAV capsid protein coding sequence is at least 90% identical to SEQ ID NO:2 or SEQ ID NO:3.

3. The nucleic acid of claim 1, wherein the nucleic acid is a plasmid, phage, viral vector, bacterial artificial chromosome, or yeast artificial chromosome.

4. The nucleic acid of claim 1, wherein the nucleic acid is an AAV vector comprising the coding sequence.

5. The nucleic acid of claim 1, wherein the nucleic acid further comprises an AAV rep coding sequence.

6. A cell in vitro comprising the nucleic acid of claim 1 stably incorporated into the genome.

7. A virus particle comprising the nucleic acid of claim 1.

8. The virus particle of claim 7, wherein the virus particle is an AAV particle, an adenovirus particle, a herpesvirus particle, or a baculovirus particle.

9. A method of producing a recombinant AAV particle comprising an AAV capsid, the method comprising:
   providing a cell in vitro with a nucleic acid according to claim 1, an AAV rep coding sequence, an AAV vector genome comprising a heterologous nucleic acid, and helper functions for generating a productive AAV infection; and
   allowing assembly of the recombinant AAV particle comprising the AAV capsid and encapsidating the AAV vector genome.

10. The nucleic acid of claim 1, wherein the encoded AAV capsid protein confers liver tropism to an AAV vector.

11. The nucleic acid of claim 1, wherein the AAV capsid protein coding sequence is at least 95% 96%, 97%, 98%, 99%, 99.1%, 99.2%, 99.3%, 99.4%, 99.5%, 99.6%, 99.7%, 99.8%, or 99.9% identical to SEQ ID NO:2 or SEQ ID NO:3.

12. The nucleic acid of claim 1, wherein the AAV capsid protein coding sequence is SEQ ID NO:2 or SEQ ID NO:3.

13. The nucleic acid of claim 12, wherein the AAV capsid protein coding sequence is SEQ ID NO:2.

14. The nucleic acid of claim 12, wherein the AAV capsid protein coding sequence is SEQ ID NO 3.

15. An AAV capsid protein comprising an amino acid sequence at least 99% identical to SEQ ID NO:5.

16. The AAV capsid protein of claim 15, comprising the amino acid sequence of SEQ ID NO:5.

17. The AAV capsid protein of claim 15 covalently linked, bound to, or encapsidating a compound selected from the group consisting of a DNA molecule, an RNA molecule, a polypeptide, a carbohydrate, a lipid, and a small organic molecule.

18. The AAV capsid protein of claim 15 that consists of: amino acid sequence of SEQ ID NO:5.

19. An AAV capsid comprising the AAV capsid protein of any one of claims 15, 16, or 18.

20. An AAV particle comprising:
   an AAV vector genome; and
   the AAV capsid of claim 19, wherein the AAV capsid encapsidates the AAV vector genome.

21. The AAV particle of claim 20, wherein the AAV vector genome comprises a heterologous nucleic acid of interest.

22. The AAV particle of claim 21, wherein the heterologous nucleic acid encodes an antisense RNA, microRNA, or RNAi.

23. The AAV particle of claim 21, wherein the heterologous nucleic acid encodes a polypeptide.

24. A pharmaceutical formulation comprising the AAV particle of claim 20 in a pharmaceutically acceptable carrier.

25. A method of delivering a nucleic acid of interest to a hepatocyte, the method comprising contacting the hepatocyte with the AAV particle of claim 21.

26. A method of delivering a nucleic acid of interest to a hepatocyte in a mammalian subject, the method comprising:
   administering an effective amount of the AAV particle of claim 21 to a mammalian subject, thereby delivering the nucleic acid of interest to a hepatocyte in the mammalian subject.

27. A method of treating a disorder in a mammalian subject in need thereof, wherein the disorder is treatable by expressing a product in the liver of the subject, the method comprising administering to the mammalian subject a therapeutically effective amount of the AAV particle of claim 20 that expresses the product, wherein the product is expressed in the mammalian subject, to thereby treat the disorder.

28. The method of claim 27, wherein the disorder is selected from the group consisting of Type Ia Glycogen storage disease (GSD), Type Ib GSD, Type Ic GSD, Type Id GSD, Type II GSD, Pompe disease, infantile Type IIa GSD and Type IIb, Type IIIa and IIIb GSD, Type IV GSD (Andersen's disease), Type V GSD (McArdle disease), Type VI GSD (Hers' disease), Type VII GSD (Tarui's disease), GSD Type VIII/IXa, GSD Type IXb, GSD Type IXc, GSD Type IXd, GSD 0, Fanconi-Bickel syndrome, phosphoglucoisomerase deficiency, muscle phosphoglycerate kinase deficiency, phosphoglycerate mutase deficiency, fructose 1,6-diphosphatase deficiency, phosphoenolpyruvate carboxykinase deficiency, lactate dehydrogenase deficiency, Hurler's Syndrome, Scheie's Syndrome, and Hurler-Scheie Syndrome, Hunter's Syndrome, Sanfilippo A Syndrome, Sanfilippo Syndrome, Morquio disease, Maroteaux-lmay disease, Sly Syndrome, hyaluronidase deficiency, sialidosis, mucolipidosis, GM1 gangliosidosis, GM2 gangliosidosis, Niemann-Pick disease, Gaucher's disease, Farber's disease, Fabry's disease, Krabbe's disease, metachromatic leukodystrophy, Wolman's disease, Batten disease, sialidosis, galactosialidosis, α-mannosidosis, β-mannosidosis, fucosidosis, sialuria, and phenylketonuria.

29. The method of claim 27, wherein the administering is by injection into the liver, injection into the portal vein, or any combination thereof.

30. The method of claim 27, wherein the product is encoded by a nucleic acid of interest operably linked to an RNA polymerase 11-based or RNA polymerase III-based promoter.

31. The method of claim 30, wherein the RNA polymerase II-based or RNA polymerase III-based promoter is a constitutive promoter.

32. The method of claim 31, wherein the RNA polymerase II-based or RNA polymerase III-based promoter is an inducible promoter.

33. The method of claim 27, wherein the product is encoded by a nucleic acid of interest operably linked to a liver-specific or liver-preferred promoter.

34. The method of claim 33, wherein the liver-specific or liver-preferred promoter is a promoter from apolipoprotein AII, albumin, alpha 1-antitrypsin, thyroxine-binding globulin, cytochrome P450 CYP3A4, or microRNA122 or a synthetic liver-specific regulatory sequence.

35. The method of claim 27, wherein the mammalian subject is human.

* * * * *

UNITED STATES PATENT AND TRADEMARK OFFICE
CERTIFICATE OF CORRECTION

PATENT NO. : 12,410,441 B2
APPLICATION NO. : 16/972938
DATED : September 9, 2025
INVENTOR(S) : Xiao et al.

It is certified that error appears in the above-identified patent and that said Letters Patent is hereby corrected as shown below:

In the Specification

Column 15, Line 37: Please correct "R2-adrenergic" to read --β2-adrenergic--

Column 19, Line 57: Please correct "www.nebi.nlm.nih.gov/BLAST" to read --www.ncbi.nlm.nih.gov/BLAST--

Column 20, Lines 66-67: Please correct "(1991) 1 Exp. Med." to read --(1991) J. Exp. Med.--

Column 21, Line 3: Please correct "β-15" to read --P-15--

Column 26, Line 66: Please correct "107" to read --$10^7$--

Column 29, Line 27: Please correct "[α-galactosidase]and" to read --[α-galactosidase] and--

Column 29, Lines 30-31: Please correct "al-antitrypsin" to read --α1-antitrypsin--

Column 30, Line 27: Please correct "(0-glucuronidase)" to read --(β-glucuronidase)--

Column 38, Line 22: Please correct "$10^6(10):3946$" to read --106(10):3946--

Column 42, Line 14: Please correct "$10^6(10):3946$" to read --106(10):3946--

In the Claims

Columns 69, Line 49- Column 71, Line 7: Please delete Claims 9-27 and replace with the following:
9. The nucleic acid of claim 1, wherein the encoded AAV capsid protein confers liver tropism to an AAV vector.

Signed and Sealed this
Thirtieth Day of December, 2025

John A. Squires
*Director of the United States Patent and Trademark Office*

10. The nucleic acid of claim 1, wherein the AAV capsid protein coding sequence is at least 95%, 96%, 97%, 98%, 99%, 99.1%, 99.2%, 99.3%, 99.4%, 99.5%, 99.6%, 99.7%, 99.8%, or 99.9% identical to SEQ ID NO:2 or SEQ ID NO:3.

11. The nucleic acid of claim 1, wherein the AAV capsid protein coding sequence is SEQ ID NO:2 or SEQ ID NO:3.

12. The nucleic acid of claim 11, wherein the AAV capsid protein coding sequence is SEQ ID NO:2.

13. The nucleic acid of claim 11, wherein the AAV capsid protein coding sequence is SEQ ID NO:3.

14. An AAV capsid protein comprising an amino acid sequence at least 99% identical to SEQ ID NO:5.

15. The AAV capsid protein of claim 14, comprising the amino acid sequence of SEQ ID NO:5.

16. The AAV capsid protein of claim 14 covalently linked, bound to, or encapsidating a compound selected from the group consisting of a DNA molecule, an RNA molecule, a polypeptide, a carbohydrate, a lipid, and a small organic molecule.

17. The AAV capsid protein of claim 14 that consists of: amino acid sequence of SEQ ID NO:5.

18. An AAV capsid comprising the AAV capsid protein of any one of claims 14, 15, or 17.

19. An AAV particle comprising:
an AAV vector genome; and
the AAV capsid of claim 18, wherein the AAV capsid encapsidates the AAV vector genome.

20. The AAV particle of claim 19, wherein the AAV vector genome comprises a heterologous nucleic acid of interest.

21. The AAV particle of claim 20, wherein the heterologous nucleic acid encodes an antisense RNA, microRNA, or RNAi.

22. The AAV particle of claim 20, wherein the heterologous nucleic acid encodes a polypeptide.

23. A pharmaceutical formulation comprising the AAV particle of claim 19 in a pharmaceutically acceptable carrier.

24. A method of delivering a nucleic acid of interest to a hepatocyte, the method comprising contacting the hepatocyte with the AAV particle of claim 20.

25. A method of producing a recombinant AAV particle comprising an AAV capsid, the method comprising:
providing a cell *in vitro* with a nucleic acid according to claim 1 or 11, an AAV rep coding sequence, an AAV vector genome comprising a heterologous nucleic acid, and helper functions for generating a productive AAV infection; and
allowing assembly of the recombinant AAV particle comprising the AAV capsid and encapsidating the AAV vector genome.

26. A method of delivering a nucleic acid of interest to a hepatocyte in a mammalian subject, the method comprising:

CERTIFICATE OF CORRECTION (continued)
U.S. Pat. No. 12,410,441 B2 administering an effective amount of the AAV particle of claim 20 to a mammalian subject, thereby delivering the nucleic acid of interest to a hepatocyte in the mammalian subject.

27. A method of treating a disorder in a mammalian subject in need thereof, wherein the disorder is treatable by expressing a product in the liver of the subject, the method comprising administering to the mammalian subject a therapeutically effective amount of the AAV particle of claim 19 that expresses the product, wherein the product is expressed in the mammalian subject, to thereby treat the disorder.

Column 72, Line 14, Claim 32: Please correct "claim 31" to read --claim 30--

SEQUENCE LISTING

<160> NUMBER OF SEQ ID NOS: 8

<210> SEQ ID NO 1
<211> LENGTH: 2214
<212> TYPE: DNA
<213> ORGANISM: Artificial
<220> FEATURE:
<223> OTHER INFORMATION: AAVXL12 capsid gene DNA sequence

<400> SEQUENCE: 1

```
atggctgccg atggttatct tccagattgg ctcgaggaca acctctctga gggcattcgc      60
gagtggtggg cgctgaaacc tggagccccg aagcccaaag ccaaccagca aaagcaggac     120
gacggccggg gtctggtgct tcctggctac aagtacctcg acccttcaa cggactcgac      180 aagggggagc ccgtcaacgc ggcggacgca gcggccctgg agcacgacaa ggcctacgac     240
cagcagctgc aggcgggtga caatccgtac ctgcggtata ccacgccga cgccgagttt     300 caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga accggtaga gccatcaccc cagcgttctc cagactcctc tacgggcatc      480
ggcaagaaag ccaacagcc cgccagaaaa agactcaatt ttggtcagac tggcgactca     540
gagtcagttc cagaccctca acctctcgga gaacctccag cagcgccctc tggtgtggga     600
cctaatacaa tggcttcagg cggtggcgca ccaatggcag acaataacga aggcgcctcc     660
ggagtgggta tgcctcagg aaattggcat tgcgattcca catggctggg cgacagagtc     720
atcaccacca gcacccgaac atgggccttg cccacctaca caatcacct ctacaagcaa      780 atctccagtg cttcaacggg ggccagcaac gacaaccact acttcggcta cagcaccccc     840
tgggggtatt ttgatttcaa cagattccac tgccactttt caccacgtga ctggcagcga     900
ctcatcaaca caattgggg attccggccc aagagactca acttcaaact cttcaacatc      960
caagtcaagg aggtcacgac gaatgatggc gtcacgacca tcgctaataa ccttaccagc    1020
acggttcaag tcttctcgga ctcggagtac cagttgccgt acgtcctcgg ctctgcgcac    1080
cagggctgcc tccctccgtt cccggcggac gtgttcatga ttccgcagta cggctaccta    1140
acgctcaaca atggcagcca ggcagtggga cggtcatcct tttactgcct ggaatatttc    1200
ccatcgcaga tgctgagaac gggcaacaac tttaccttca gctacacctt tgaggaagtg    1260 ccttttccaca gcagctacgc gcacagccag agcctggacc ggctgatgaa tcctctcatc    1320
gaccaatacc tgtattacct gaacagaact caaaatcagt ccggaagtgc ccaaaacaag    1380
gacttgctgt ttagccgtgg gtctccagct ggcatgtctg ttcagcccaa aaactggcta    1440
cctggaccct gttaccggca gcagcgcgtt tctaaaacaa aaacagacaa caacaacagc    1500
aactttacct ggactggtgc ttcaaaatat aaccttaatg ggcgtgaatc tataatcaac    1560
cctggcactg ctatggcctc acacaaagac gacaaagaca agttcttcc catgagcggt    1620 gtcatgattt ttggaaagga gagcgccgga gcttcaaaca ctgcattgga caatgtcatg    1680
```

-continued

| | |
|---|---|
| atcacagacg aagaggaaat caaagccact aaccccgtgg ccaccgaaag atttgggact | 1740 |
| gtggcagtca atctccagag cagcagcaca gaccctgcga ccggagatgt gcatgttatg | 1800 |
| ggagccttac ctggaatggt gtggcaagac agagacgtat acctgcaggg tcctatttgg | 1860 |
| gccaaaattc ctcacacgga tggacacttt cacccgtctc ctcttatggg cggctttgga | 1920 |
| ctcaagaacc cgcctcctca gatcctcatc aaaaacacgc tgttcctgc gaatcctccg | 1980 |
| gcagagtttt cggctacaaa gtttgcttca ttcatcaccc agtattccac aggacaagtg | 2040 |
| agcgtggaga ttgaatggga gctgcagaaa gaaaacagca aacgctggaa tcccgaagtg | 2100 |
| cagtatacat ctaactatgc aaaatctgcc aacgttgatt tcactgtgga caacaatgga | 2160 |
| ctttatactg agcctcgccc cattggcacc cgttacctca cccgtcccct gtaa | 2214 |

<210> SEQ ID NO 2
<211> LENGTH: 2214
<212> TYPE: DNA
<213> ORGANISM: Artificial
<220> FEATURE:
<223> OTHER INFORMATION: AAVXL32 capsid gene DNA sequence

<400> SEQUENCE: 2

| | |
|---|---|
| atggctgccg atggttatct tccagattgg ctcgaggaca acctctctga gggcattcgc | 60 |
| gagtggtggg cgctgaaacc tggagccccg aagcccaaag ccaaccagca aaagcaggac | 120 |
| gacggccggg gtctggtgct tcctggctac aagtacctcg gacccttcaa cggactcgac | 180 |
| aagggggagc ccgtcaacgc ggcggacgca gcggccctgg agcacgacaa ggcctacgac | 240 |
| cagcagctgc aggcgggtga caatccgtac ctgcggtata ccacgccga cgccgagttt | 300 |
| caggagcgtc tgcaagaaga tacgtctttt ggggcaacc tcgggcgagc agtcttccag | 360 |
| gccaagaagc gggttctcga acctctcggt ctggttgagg aaggcgctaa gacggctcct | 420 |
| ggaaagaaga gaccggtaga gccatcaccc cagcgttctc cagactcctc tacgggcatc | 480 |
| ggcaagaaag gccaacagcc cgccagaaaa agactcaatt ttggtcagac tggcgactca | 540 |
| gagtcagttc cagaccctca acctctcgga gaacctccag cagcgccctc tggtgtggga | 600 |
| cctaatacaa tggcttcagg cggtggcgca ccaatggcag acaataacga aggcgccgac | 660 |
| ggagtgggta tgcctcagg aaattggcat gcgattcca catggctggg cgacagagtc | 720 |
| atcaccacca gcacccgaac atgggccttg cccacctata caaccacct ctacaagcaa | 780 |
| atctccagtg cttcaacggg ggccagcaac gacaaccact acttcggcta cagcaccccc | 840 |
| tgggggtatt ttgatttcaa cagattccac tgccatttct caccacgtga ctggcagcga | 900 |
| ctcatcaaca caattggggg attccggccc aagagactca acttcaagct cttcaacatc | 960 |
| caagtcaagg aggtcacgac gaatgatggc gtcacgacca tcgctaataa ccttaccagc | 1020 |
| acggttcaag tcttctcgga ctcggagtac cagttgccgt acgtcctcgg ctctgcgcac | 1080 |
| cagggctgcc tccctccgtt cccggcggac gtgttcatga ttccgcaata cggctacctg | 1140 |
| acgctcaaca atggcagcca agccgtggga cgttcatcct tttactgcct ggaatatttc | 1200 |
| ccttctcaga tgctgagaac gggcaacaac tttaccttca gctacacctt tgaggaagtg | 1260 |
| cctttccaca gcagctacgc gcacagccag agcctggacc ggctgatgaa tcctctcatc | 1320 |
| gaccagtacc tgtattacct gaacagaact cagaatcagt ccggaagtgc ccaaaacaag | 1380 |
| gacttgctgt ttagccgtgg gtctccagct ggcatgtctg ttcagccaa aaactggcta | 1440 |
| cctggaccct gttaccggca gcagcgcgtt tctaaaacaa aaacagacaa caacaacagc | 1500 |

-continued

| | |
|---|---|
| aactttacct ggactggtgc ttcaaaatat aacctcaatg ggcgtgaatc catcatcaac | 1560 |
| cctggcactg ctatggcctc acacaaagac gacaaagaca agttctttcc catgagcggt | 1620 |
| gtcatgattt ttggaaagga gagcgccgga gcttcaaaca ctgcattgga caatgtcatg | 1680 |
| atcacagacg aagaggaaat caaagccact aaccccgtgg ccaccgaaag atttgggact | 1740 |
| gtggcagtca atctccagag cagcagcaca gaccctgcga ccggagatgt gcatgttatg | 1800 |
| ggagccttac ctggaatggt gtggcaagac agagacgtat acctgcaggg tcctatttgg | 1860 |
| gccaaaattc ctcacacgga tggacacttt cacccgtctc ctctcatggg cggcttttgga | 1920 |
| cttaagcacc cgcctcctca gatcctcatc aaaaacacgc ctgttcctgc gaatcctccg | 1980 |
| gcagagtttt cggctacaaa gtttgcttca ttcatcaccc agtattccac aggacaagtg | 2040 |
| agcgtggaga ttgaatggga gctgcagaaa gaaaacagca aacgctggaa tcccgaagtg | 2100 |
| cagtatacat ctaactatgc aaaatctgcc aacgttgatt ttactgtgga caacaatgga | 2160 |
| ctttatactg agcctcgccc cattggcacc cgttacctca cccgtcccct gtaa | 2214 |

<210> SEQ ID NO 3
<211> LENGTH: 2214
<212> TYPE: DNA
<213> ORGANISM: Artificial
<220> FEATURE:
<223> OTHER INFORMATION: AAVXL32.1 capsid gene DNA sequence

<400> SEQUENCE: 3

| | |
|---|---|
| atggctgccg atggttatct tccagattgg ctcgaggaca acctctctga gggcattcgc | 60 |
| gagtggtggg cgctgaaacc tggagccccg aagcccaaag ccaaccagca aaagcaggac | 120 |
| gacggccggg gtctggtgct tcctggctac aagtacctcg acccttcaa cggactcgac | 180 |
| aaggggagc ccgtcaacgc ggcggacgca gcggccctcg agcacgacaa ggcctacgac | 240 |
| cagcagctgc aggcgggtga caatccgtac ctgcggtata ccacgccga cgccgagttt | 300 |
| caggagcgtc tgcaagaaga tacgtctttt gggggcaacc tcgggcgagc agtcttccag | 360 |
| gccaagaagc gggttctcga acctctcggt ctggttgagg aaggcgctaa gacggctcct | 420 |
| ggaaagaaga gaccggtaga gccatcaccc agcgttctc cagactcctc tacgggcatc | 480 |
| ggcaagaaag gccaacagcc cgccagaaaa agactcaatt ttggtcagac tggcgactca | 540 |
| gagtcagttc cagaccctca acctctcgga gaacctccag cagcgccctc tggtgtggga | 600 |
| cctaatacaa tggcttcagg cggtggcgca ccaatggcag acaataacga aggcgccgac | 660 |
| ggagtgggta tgcctcagg aaattggcat gcgattcca catggctggg cgacagagtc | 720 |
| atcaccacca gcacccgaac atgggccttg cccacctata caaccacct ctacaagcaa | 780 |
| atctccagtg cttcaacggg ggccagcaac gacaaccact acttcggcta cagcaccccc | 840 |
| tgggggtatt ttgatttcaa cagattccac tgccatttct caccacgtga ctggcagcga | 900 |
| ctcatcaaca caattgggg attccggccc aagagactca acttcaagct cttcaacatc | 960 |
| caagtcaagg aggtcacgac gaatgatggc gtcacgacca tcgctaataa ccttaccagc | 1020 |
| acggttcaag tcttctcgga ctcggagtac cagttgccgt acgtcctcgg ctctgcgcac | 1080 |
| cagggctgcc tccctccgtt cccggcggac gtgttcatga ttccgcaata cggctacctg | 1140 |
| acgctcaaca atggcagcca agccgtggga cgttcatcct ttactgcct ggaatatttc | 1200 |
| ccttctcaga tgctgagaac gggcaacaac tttaccttca gctacacctt tgaggaagtg | 1260 |
| cctttccaca gcagctacgc gcacagccag agcctggacc ggctgatgaa tcctctcatc | 1320 |
| gaccagtacc tgtattacct gaacagaact cagaatcagt ccggaagtgc ccaaaacaag | 1380 |

-continued

```
gacttgctgt ttagccgtgg gtctccagct ggcatgtctg ttcagcccaa aaactggcta    1440
cctggaccct gttaccggca gcagcgcgtt tctaaaacaa aaacagacaa caacaacagc    1500
aactttacct ggactggtgc ttcaaaatat aacctcaatg ggcgtgaatc catcatcaac    1560
cctggcactg ctatggcctc acacaaagac gacaaagaca agttctttcc catgagcggt    1620
gtcatgattt ttggaaagga gagcgccgga gcttcaaaca ctgcattgga caatgtcatg    1680
atcacagacg aagaggaaat caaagccact aaccccgtgg ccaccgaaag atttgggact    1740
gtggcagtca atctccagag cagcagcaca gaccctgcga ccggagatgt gcatgttatg    1800
ggagccttac ctggaatggt gtggcaagac agagacgtat acctgcaggg tcctatttgg    1860
gccaaaattc ctcacacgga tggacacttt cacccgtctc ctctcatggg cggctttgga    1920
cttaagcacc cgcctcctca gatcctcatc aaaaacacgc ctgttcctgc gaatcctccg    1980
gcagagtttt cggctacaaa gtttgcttca ttcatcaccc agtattccac aggacaagtg    2040
agcgtggaga ttgaatggga gctgcagaaa gaaaacagca aacgctggaa tcccgaagtg    2100
cagtatacat ctaactatgc aaaatctgcc aacgttgatt ttactgtgga caacaatgga    2160
ctttatactg agcctcgccc cattggcacc cgttacctca cccgtcccct gtaa          2214
```

<210> SEQ ID NO 4
<211> LENGTH: 737
<212> TYPE: PRT
<213> ORGANISM: Artificial
<220> FEATURE:
<223> OTHER INFORMATION: AAVXL12 capsid amino acid sequence

<400> SEQUENCE: 4

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ser Gly Gly
        195                 200                 205

Gly Ala Pro Met Ala Asp Asn Asn Glu Gly Ala Ser Gly Val Gly Asn
```

```
            210                 215                 220
Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
                260                 265                 270

His Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
                340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Glu Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Asn
            435                 440                 445

Arg Thr Gln Asn Gln Ser Gly Ser Ala Gln Asn Lys Asp Leu Leu Phe
            450                 455                 460

Ser Arg Gly Ser Pro Ala Gly Met Ser Val Gln Pro Lys Asn Trp Leu
465                 470                 475                 480

Pro Gly Pro Cys Tyr Arg Gln Gln Arg Val Ser Lys Thr Lys Thr Asp
                485                 490                 495

Asn Asn Asn Ser Asn Phe Thr Trp Thr Gly Ala Ser Lys Tyr Asn Leu
                500                 505                 510

Asn Gly Arg Glu Ser Ile Ile Asn Pro Gly Thr Ala Met Ala Ser His
            515                 520                 525

Lys Asp Asp Lys Asp Lys Phe Phe Pro Met Ser Gly Val Met Ile Phe
            530                 535                 540

Gly Lys Glu Ser Ala Gly Ala Ser Asn Thr Ala Leu Asp Asn Val Met
545                 550                 555                 560

Ile Thr Asp Glu Glu Glu Ile Lys Ala Thr Asn Pro Val Ala Thr Glu
                565                 570                 575

Arg Phe Gly Thr Val Ala Val Asn Leu Gln Ser Ser Ser Thr Asp Pro
                580                 585                 590

Ala Thr Gly Asp Val His Val Met Gly Ala Leu Pro Gly Met Val Trp
            595                 600                 605

Gln Asp Arg Asp Val Tyr Leu Gln Gly Pro Ile Trp Ala Lys Ile Pro
            610                 615                 620

His Thr Asp Gly His Phe His Pro Ser Pro Leu Met Gly Gly Phe Gly
625                 630                 635                 640
```

Leu Lys Asn Pro Pro Gln Ile Leu Ile Lys Asn Thr Pro Val Pro
            645             650             655

Ala Asn Pro Pro Ala Glu Phe Ser Ala Thr Lys Phe Ala Ser Phe Ile
        660             665             670

Thr Gln Tyr Ser Thr Gly Gln Val Ser Val Glu Ile Glu Trp Glu Leu
            675             680             685

Gln Lys Glu Asn Ser Lys Arg Trp Asn Pro Glu Val Gln Tyr Thr Ser
        690             695             700

Asn Tyr Ala Lys Ser Ala Asn Val Asp Phe Thr Val Asp Asn Asn Gly
705             710             715             720

Leu Tyr Thr Glu Pro Arg Pro Ile Gly Thr Arg Tyr Leu Thr Arg Pro
            725             730             735

Leu

<210> SEQ ID NO 5
<211> LENGTH: 737
<212> TYPE: PRT
<213> ORGANISM: Artificial
<220> FEATURE:
<223> OTHER INFORMATION: AAVXL32 capsid amino acid sequence

<400> SEQUENCE: 5

Met Ala Ala Asp Gly Tyr Leu Pro Asp Trp Leu Glu Asp Asn Leu Ser
1               5               10              15

Glu Gly Ile Arg Glu Trp Trp Ala Leu Lys Pro Gly Ala Pro Lys Pro
            20              25              30

Lys Ala Asn Gln Gln Lys Gln Asp Asp Gly Arg Gly Leu Val Leu Pro
        35              40              45

Gly Tyr Lys Tyr Leu Gly Pro Phe Asn Gly Leu Asp Lys Gly Glu Pro
    50              55              60

Val Asn Ala Ala Asp Ala Ala Ala Leu Glu His Asp Lys Ala Tyr Asp
65              70              75              80

Gln Gln Leu Gln Ala Gly Asp Asn Pro Tyr Leu Arg Tyr Asn His Ala
            85              90              95

Asp Ala Glu Phe Gln Glu Arg Leu Gln Glu Asp Thr Ser Phe Gly Gly
        100             105             110

Asn Leu Gly Arg Ala Val Phe Gln Ala Lys Lys Arg Val Leu Glu Pro
    115             120             125

Leu Gly Leu Val Glu Glu Gly Ala Lys Thr Ala Pro Gly Lys Lys Arg
130             135             140

Pro Val Glu Pro Ser Pro Gln Arg Ser Pro Asp Ser Ser Thr Gly Ile
145             150             155             160

Gly Lys Lys Gly Gln Gln Pro Ala Arg Lys Arg Leu Asn Phe Gly Gln
            165             170             175

Thr Gly Asp Ser Glu Ser Val Pro Asp Pro Gln Pro Leu Gly Glu Pro
        180             185             190

Pro Ala Ala Pro Ser Gly Val Gly Pro Asn Thr Met Ala Ser Gly Gly
    195             200             205

Gly Ala Pro Met Ala Asp Asn Asn Glu Gly Ala Asp Gly Val Gly Asn
    210             215             220

Ala Ser Gly Asn Trp His Cys Asp Ser Thr Trp Leu Gly Asp Arg Val
225             230             235             240

Ile Thr Thr Ser Thr Arg Thr Trp Ala Leu Pro Thr Tyr Asn Asn His
            245             250             255

```
Leu Tyr Lys Gln Ile Ser Ser Ala Ser Thr Gly Ala Ser Asn Asp Asn
                260                 265                 270

His Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Glu Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Asn
        435                 440                 445

Arg Thr Gln Asn Gln Ser Gly Ser Ala Gln Asn Lys Asp Leu Leu Phe
        450                 455                 460

Ser Arg Gly Ser Pro Ala Gly Met Ser Val Gln Pro Lys Asn Trp Leu
465                 470                 475                 480

Pro Gly Pro Cys Tyr Arg Gln Gln Arg Val Ser Lys Thr Lys Thr Asp
                485                 490                 495

Asn Asn Asn Ser Asn Phe Thr Trp Thr Gly Ala Ser Lys Tyr Asn Leu
            500                 505                 510

Asn Gly Arg Glu Ser Ile Ile Asn Pro Gly Thr Ala Met Ala Ser His
        515                 520                 525

Lys Asp Asp Lys Asp Lys Phe Phe Pro Met Ser Gly Val Met Ile Phe
        530                 535                 540

Gly Lys Glu Ser Ala Gly Ala Ser Asn Thr Ala Leu Asp Asn Val Met
545                 550                 555                 560

Ile Thr Asp Glu Glu Glu Ile Lys Ala Thr Asn Pro Val Ala Thr Glu
                565                 570                 575

Arg Phe Gly Thr Val Ala Val Asn Leu Gln Ser Ser Ser Thr Asp Pro
            580                 585                 590

Ala Thr Gly Asp Val His Val Met Gly Ala Leu Pro Gly Met Val Trp
        595                 600                 605

Gln Asp Arg Asp Val Tyr Leu Gln Gly Pro Ile Trp Ala Lys Ile Pro
        610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Ala Glu Phe Ser Ala Thr Lys Phe Ala Ser Phe Ile
            660                 665                 670

Thr Gln Tyr Ser Thr Gly Gln Val Ser Val Glu Ile Glu Trp Glu Leu
```

```
                675                 680                 685
Gln Lys Glu Asn Ser Lys Arg Trp Asn Pro Glu Val Gln Tyr Thr Ser
    690                 695                 700

Asn Tyr Ala Lys Ser Ala Asn Val Asp Phe Thr Val Asp Asn Asn Gly
705                 710                 715                 720

Leu Tyr Thr Glu Pro Arg Pro Ile Gly Thr Arg Tyr Leu Thr Arg Pro
                725                 730                 735

Leu

<210> SEQ ID NO 6
<211> LENGTH: 737
<212> TYPE: PRT
<213> ORGANISM: Artificial
<220> FEATURE:
<223> OTHER INFORMATION: AAV XL32.1 capsid amino acid sequence

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ser Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Thr Gly Ala Ser Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300
```

```
Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Ile Ala Asn
            325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
            405                 410                 415

Phe Glu Glu Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Asn
            435                 440                 445

Arg Thr Gln Asn Gln Ser Gly Ser Ala Gln Asn Lys Asp Leu Leu Phe
450                 455                 460

Ser Arg Gly Ser Pro Ala Gly Met Ser Val Gln Pro Lys Asn Trp Leu
465                 470                 475                 480

Pro Gly Pro Cys Tyr Arg Gln Gln Arg Val Ser Lys Thr Lys Thr Asp
            485                 490                 495

Asn Asn Asn Ser Asn Phe Thr Trp Thr Gly Ala Ser Lys Tyr Asn Leu
            500                 505                 510

Asn Gly Arg Glu Ser Ile Ile Asn Pro Gly Thr Ala Met Ala Ser His
            515                 520                 525

Lys Asp Asp Lys Asp Lys Phe Phe Pro Met Ser Gly Val Met Ile Phe
530                 535                 540

Gly Lys Glu Ser Ala Gly Ala Ser Asn Thr Ala Leu Asp Asn Val Met
545                 550                 555                 560

Ile Thr Asp Glu Glu Ile Lys Ala Thr Asn Pro Val Ala Thr Glu
            565                 570                 575

Arg Phe Gly Thr Val Ala Val Asn Leu Gln Ser Ser Ser Thr Asp Pro
            580                 585                 590

Ala Thr Gly Asp Val His Val Met Gly Ala Leu Pro Gly Met Val Trp
            595                 600                 605

Gln Asp Arg Asp Val Tyr Leu Gln Gly Pro Ile Trp Ala Lys Ile Pro
            610                 615                 620

His Thr Asp Gly His Phe His Pro Ser Pro Leu Met Gly Gly Phe Gly
625                 630                 635                 640

Leu Lys His Pro Pro Pro Gln Ile Leu Ile Lys Asn Thr Pro Val Pro
            645                 650                 655

Ala Asn Pro Pro Ala Glu Phe Ser Ala Thr Lys Phe Ala Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Val Gln Tyr Thr Ser
            690                 695                 700

Asn Tyr Ala Lys Ser Ala Asn Val Asp Phe Thr Val Asp Asn Asn Gly
705                 710                 715                 720
```

```
Leu Tyr Thr Glu Pro Arg Pro Ile Gly Thr Arg Tyr Leu Thr Arg Pro
            725                 730                 735
Leu

<210> SEQ ID NO 7
<211> LENGTH: 35
<212> TYPE: DNA
<213> ORGANISM: Artificial
<220> FEATURE:
<223> OTHER INFORMATION: DNA Primer CAP-5'

<400> SEQUENCE: 7
cccaagcttc gatcaactac gcagacaggt accaa                              35

<210> SEQ ID NO 8
<211> LENGTH: 41
<212> TYPE: DNA
<213> ORGANISM: Artificial
<220> FEATURE:
<223> OTHER INFORMATION: DNA Primer CAP-3'

<400> SEQUENCE: 8
ataagaatgc ggccgcagag accaaagttc aactgaaacg a                       41
```